United States Patent
Alminana Domenech et al.

(10) Patent No.: US 10,799,442 B2
(45) Date of Patent: Oct. 13, 2020

(54) COMPOUNDS USEFUL IN THE TREATMENT AND/OR CARE OF THE SKIN, HAIR, NAILS, AND/OR MUCOUS MEMBRANES

(71) Applicant: LUBRIZOL ADVANCED MATERIALS, INC., Cleveland, OH (US)

(72) Inventors: Nuria Alminana Domenech, Barcelona (ES); Wim Van Den Nest, Barcelona (ES); Maria Del Carmen Lidon, Barcelona (ES); Antonio Ferrer Montiel, Alicante (ES)

(73) Assignee: LUBRIZOL ADVANCED MATERIALS, INC., Cleveland, OH (US)

( * ) Notice: Subject to any disclaimer, the term of this patent is extended or adjusted under 35 U.S.C. 154(b) by 0 days.

(21) Appl. No.: 16/060,476

(22) PCT Filed: Dec. 8, 2016

(86) PCT No.: PCT/US2016/065568
§ 371 (c)(1),
(2) Date: Jun. 8, 2018

(87) PCT Pub. No.: WO2017/100421
PCT Pub. Date: Jun. 15, 2017

(65) Prior Publication Data
US 2018/0369115 A1 Dec. 27, 2018

(30) Foreign Application Priority Data
Dec. 10, 2015 (EP) .................................... 15382614

(51) Int. Cl.
| | |
|---|---|
| *A61K 8/64* | (2006.01) |
| *A61Q 19/08* | (2006.01) |
| *A61K 9/00* | (2006.01) |
| *A61K 9/107* | (2006.01) |
| *A61K 9/127* | (2006.01) |
| *C07K 7/06* | (2006.01) |
| *A61Q 19/00* | (2006.01) |
| *A61P 17/02* | (2006.01) |
| *A61K 38/08* | (2019.01) |
| *A61K 38/00* | (2006.01) |

(52) U.S. Cl.
CPC .............. *A61K 8/64* (2013.01); *A61K 9/0014* (2013.01); *A61K 9/1075* (2013.01); *A61K 9/1272* (2013.01); *A61K 38/08* (2013.01); *A61P 17/02* (2018.01); *A61Q 19/00* (2013.01); *A61Q 19/08* (2013.01); *C07K 7/06* (2013.01); *A61K 38/00* (2013.01)

(58) Field of Classification Search
None
See application file for complete search history.

(56) References Cited

U.S. PATENT DOCUMENTS

2003/0007976 A1* 1/2003 Watson .................. A61K 39/04
424/184.1
2011/0318380 A1 12/2011 Brix et al.
2014/0120141 A1 5/2014 García Antón et al.

FOREIGN PATENT DOCUMENTS

| WO | WO2009-059972 | * | 1/2009 |
| WO | WO2010-037395 | * | 1/2010 |
| WO | WO 2010/037395 A2 | | 4/2010 |
| WO | WO 2012/130771 A1 | | 10/2012 |

OTHER PUBLICATIONS

Merck Manual teaches (<https://www.merckmanuals.com/home/digestive-disorders/gastritis-and-peptic-ulcer-disease/peptic-ulcer-disease> 2019).*
Albericio, F., et al., "Preparation and application of the 5-(4-(9-fluorenylmethyloxycarbonyl) aminomethyl-3,5-dimethoxy-phenoxy)valeric-acid (PAL) handle for the solid-phase synthesis of C-terminal peptide amides under mild conditions," J. Org. Chem., 55, 3730-3743(1990).
Atherton, B., et al., "Solid Phase Peptide Synthesis: A practical approach," IRL Oxford University Press, pp. 1-61 (1989).
Barlos, K., et al., "Darstellung geschützter Peptid-Fragmente unter Einsatz substituierter Triphenylmethyl-Harze," Tetrahedron Lett., 30, 3943-3946 (1989) English Abstract only.
Barlos, K.. et al., "Veresterung von partiell geschützten Peptid-Fragmenten mit Harzen. Einsatz von 2-Chlorotritylchlorid zur Synthese von Leu1-Gastrin I," Tetrahedron Lett., 30, 3947-3951 (1989) English Abstract only.
Berge, S.M., et al., "Pharmaceutical Salts," J. Pharm. Sci., 66, pp. 1-19 (1977).
Bodanzsky, M., et al., "The practice of Peptide Synthesis," pp. 75-126, Springer Verlag, Berlin (1994).
Christensen, T., A Qualitative Test for Monitoring Coupling Completeness in Solid Phase Peptide Synthesis Using Chloranil, Acta Chem. Scand., 33B, pp. 763-766 (1979).
Dynoodt, P., et al., "Identification of miR-145 as a key regulator of the pigmentary process," J. Invest. Dermatol., 133(1):201-9 (Jan. 2013).
Fuchs, E., "Skin stem cells: rising to the surface," J. Cell Biol., 180(2):273-284 (Jan. 28, 2008).
Gras, C., et al., "miR-145 Contributes to Hypertrophic Scarring of the Skin by Inducing Myofibroblast Activity," Mol. Med. 21:296-304 (Apr. 2015).

(Continued)

*Primary Examiner* — James H Alstrum-Acevedo
*Assistant Examiner* — Tara L Martinez
(74) *Attorney, Agent, or Firm* — Thoburn Dunlap

(57) ABSTRACT

Compounds of general formula (I): R1-Wm-Xn-AA1-AA2-AA3-AA4-AA5-AA6-Yp-Zq-R2 (I) their stereoisomers, mixtures thereof and/or their cosmetically or pharmaceutically acceptable salts, cosmetic and/or pharmaceutical compositions which contain them and their use in medicine, and in processes of treatment and/or care of the skin, hair and/or mucous membranes, in particular in the aging and photoaging of the skin.

21 Claims, No Drawings

Specification includes a Sequence Listing.

(56) References Cited

OTHER PUBLICATIONS

Hildebrand, J., et al., "A comprehensive analysis of microRNA expression during keratinocyte differentiation in vitro and in vivo," J. Invest. Dermatol., 131 91: 20-9 (2011).
Hipler, U.C, et al., "Biofunctional Textiles and the Skin" in Curr. Probl. Dermatol. v.33, pp. 35-41 (Hipler U.C. and Elsner P., eds.) S. Karger AG, Basel, Switzerland (2006).
Hofmann, J.W., et al., "Reduced expression of MYC increases longevity and enhances health span," Cell 2015, 160(3) 477-88 (Jan. 2015).
Kaiser, E., et al., Anal. Biochem., 34: 595-598 (1970).
Kullmann, W., "Proteases as catalysts for enzymic syntheses of opioid peptides," J. Biol. Chem., 255(17), pp. 8234-8238 (1980).
La Rocca, G., "Regulation of microRNA-145 by growth arrest and differentiation," Exp. Cell Res., 317(4); 488-95 (Feb. 2011).
Lin, L., et al., "Type I IFN inhibits innate IL-10 production in macrophages by downregulating microRNA-145," J. Immunol., 191(7):3896-904 (Oct. 2013).
Lin, Y.Y., "KSRP and MicroRNA 145 are negative regulators of lipolysis in white adipose tissue," Mol. Cell Biol., 34(12):2339-49 (Jun. 2014).
Lloyd-Williams, P., et al., "Chemical Approaches to the Synthesis of Peptides and Proteins," pp. 19-93, CRC, synthesis in solution, enzymatic synthesis, Boca Raton, FL, USA (1997).
Lloyd-Williams, P. et al., "Convergent Solid-Phase Peptide Synthesis," Tetrahedron, 49(48), pp. 11065-11133 (1993).
Lorente-Cebrian, S., et al., "MicroRNAs regulate human adipocyte lipolysis: effects of miR-145 are linked to TNF-α," PLoS One. ;9(1):e86800, pp. 1-10 (Jan. 2014).
Malcolm, R.K., et al., "Controlled release of a model antibacterial drug from a novel self-lubricating silicone biomaterial," J. Cont. Release, 97(2), 313-320 (2004).

Matsueda, G.R., et al., "A p-methylbenzhydrylamine resin for improved solid-phase synthesis of peptide amides," Peptides, 2, pp. 45-50 (1981).
Moll, R, et al., "The human keratins: biology and pathology," Histochem. Cell Biol., 129 60; 705-33 (Jun. 2008).
Nelson, G., "Application of microencapsulation in textiles," Int. J. Pharm., 242(1-2), pp. 55-62 (2002).
Peng, Y., et al., "Stem Cells and aberrant signaling of molecular systems in skin aging," Aging Res. Rev. pp. 8-21 (Jan. 2015).
Rink, H., "Solid-phase synthesis of protected peptide fragments using a trialkoxy-diphenyl-methylester resin," Tetrahedron Lett., 28, pp. 3787-3790 (1987).
Roberts, D.C., et al., "Unusual amino acids in peptide synthesis," in The Peptides, vol. 5 Chapter VI, pp. 341-449 (Gross E. and Meienhofer J., Eds.) Academic Press, New York, USA (1983).
Schaab, C.K., "Impregnating Fabrics with Microcapsules," Happi, pp. 84-86 (May 1986).
Stewart, J.M., et al., "Solid Phase Peptide Synthesis," 2nd edition, pp. 1-20, Pierce Chemical Company, Rockford, Illinois (1984).
Xu, N., et al., "Micro RNA-145 regulates OCT4, SOX2 and KLF4 and represses pluripotency in human embryonic stem cells," Cell, 137(4):647-658 (May 2009).
Wang, S.S., "p-Alkoxybenzyl Alcohol Resin and p-Alkoxybenzyloxycarbonylhydrazide Resin for Solid Phase Synthesis of Protected Peptide Fragments," J. Am. Chem. Soc., 95, pp. 1328-1333 (1973).
Watt, F.M., et al., "MYC in mammalian epidermis: how can an oncogene stimulate differentiation?" Nat. Rev. Cancer, 8(3); 234-42 (Mar. 2008).
Wilkinson, et al., "Harry's Cosmeticology," Seventh edition, pp. 50-73 and 757-799 (Wilkinson J.B., Moore R.J., eds.) Longman House, Essex, GB (1982).

* cited by examiner

```
                         SEQUENCE LISTING

<160> NUMBER OF SEQ ID NOS: 34

<210> SEQ ID NO 1
<211> LENGTH: 6
<212> TYPE: PRT
<213> ORGANISM: artificial sequence
<220> FEATURE:
<223> OTHER INFORMATION: synthetic peptide

<400> SEQUENCE: 1

Gln Glu Met Arg Met Gln
1               5

<210> SEQ ID NO 2
<211> LENGTH: 6
<212> TYPE: PRT
<213> ORGANISM: artificial sequence
<220> FEATURE:
<223> OTHER INFORMATION: synthetic peptide

<400> SEQUENCE: 2

Asp Glu Met Arg Met Gln
1               5

<210> SEQ ID NO 3
<211> LENGTH: 6
<212> TYPE: PRT
<213> ORGANISM: artificial sequence
<220> FEATURE:
<223> OTHER INFORMATION: synthetic peptide

<400> SEQUENCE: 3

Glu Glu Met Arg Met Gln
1               5

<210> SEQ ID NO 4
<211> LENGTH: 6
<212> TYPE: PRT
<213> ORGANISM: artificial sequence
<220> FEATURE:
<223> OTHER INFORMATION: synthetic peptide

<400> SEQUENCE: 4

Gln Gln Met Arg Met Gln
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide

<400> SEQUENCE: 5

Gln Glu Met Lys Met Gln
1               5

<210> SEQ ID NO 6
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: Xaa
```

```
<222> LOCATION: (1)..(1)
<223> OTHER INFORMATION: Xaa is Gln
<220> FEATURE:
<221> NAME/KEY: Xaa
<222> LOCATION: (2)..(2)
<223> OTHER INFORMATION: Xaa is Glu
<220> FEATURE:
<221> NAME/KEY: Xaa
<222> LOCATION: (3)..(3)
<223> OTHER INFORMATION: Xaa is Met
<220> FEATURE:
<221> NAME/KEY: Xaa
<222> LOCATION: (4)..(4)
<223> OTHER INFORMATION: Xaa is Orn
<220> FEATURE:
<221> NAME/KEY: Xaa
<222> LOCATION: (5)..(5)
<223> OTHER INFORMATION: Xaa is Met
<220> FEATURE:
<221> NAME/KEY: Xaa
<222> LOCATION: (6)..(6)
<223> OTHER INFORMATION: Xaa is Gln

<400> SEQUENCE: 6

Xaa Xaa Xaa Xaa Xaa Xaa
1               5

<210> SEQ ID NO 7
<211> LENGTH: 6
<212> TYPE: PRT
<213> ORGANISM: artificial sequence
<220> FEATURE:
<223> OTHER INFORMATION: synthetic peptide

<400> SEQUENCE: 7

Gln Glu Met Arg Met Glu
1               5

<210> SEQ ID NO 8
<211> LENGTH: 6
<212> TYPE: PRT
<213> ORGANISM: artificial sequence
<220> FEATURE:
<223> OTHER INFORMATION: synthetic peptide

<400> SEQUENCE: 8

Gln Glu Met Arg Met Asn
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Glu Glu Met Arg Met Gln
1               5

<210> SEQ ID NO 10
<211> LENGTH: 6
<212> TYPE: PRT
<213> ORGANISM: artificial sequence
<220> FEATURE:
<223> OTHER INFORMATION: synthetic peptide

<400> SEQUENCE: 10

Gln Asp Met Arg Met Gln
1               5
```

<210> SEQ ID NO 11
<211> LENGTH: 6
<212> TYPE: PRT
<213> ORGANISM: artificial sequence
<220> FEATURE:
<223> OTHER INFORMATION: synthetic peptide

<400> SEQUENCE: 11

Gln Glu Leu Arg Met Gln
1               5

<210> SEQ ID NO 12
<211> LENGTH: 6
<212> TYPE: PRT
<213> ORGANISM: artificial sequence
<220> FEATURE:
<223> OTHER INFORMATION: synthetic peptide

<400> SEQUENCE: 12

Gln Glu Ile Arg Met Gln
1               5

<210> SEQ ID NO 13
<211> LENGTH: 6
<212> TYPE: PRT
<213> ORGANISM: artificial sequence
<220> FEATURE:
<223> OTHER INFORMATION: synthetic peptide

<400> SEQUENCE: 13

Gln Glu Met Arg Ile Gln
1               5

<210> SEQ ID NO 14
<211> LENGTH: 6
<212> TYPE: PRT
<213> ORGANISM: artificial sequence
<220> FEATURE:
<223> OTHER INFORMATION: synthetic peptide

<400> SEQUENCE: 14

Gln Glu Met Arg Leu Gln
1               5

<210> SEQ ID NO 15
<211> LENGTH: 6
<212> TYPE: PRT
<213> ORGANISM: artificial sequence
<220> FEATURE:
<223> OTHER INFORMATION: synthetic peptide

<400> SEQUENCE: 15

Glu Glu Ile Arg Met Gln
1               5

<210> SEQ ID NO 16
<211> LENGTH: 6
<212> TYPE: PRT
<213> ORGANISM: artificial sequence
<220> FEATURE:
<223> OTHER INFORMATION: synthetic peptide

<400> SEQUENCE: 16

Asp Gln Met Arg Met Gln
1               5

```
<210> SEQ ID NO 17
<211> LENGTH: 6
<212> TYPE: PRT
<213> ORGANISM: artificial sequence
<220> FEATURE:
<223> OTHER INFORMATION: synthetic peptide

<400> SEQUENCE: 17

Glu Gln Met Arg Met Gln
1               5

<210> SEQ ID NO 18
<211> LENGTH: 6
<212> TYPE: PRT
<213> ORGANISM: artificial sequence
<220> FEATURE:
<223> OTHER INFORMATION: synthetic peptide

<400> SEQUENCE: 18

Gln Glu Met Lys Leu Gln
1               5

<210> SEQ ID NO 19
<211> LENGTH: 6
<212> TYPE: PRT
<213> ORGANISM: artificial sequence
<220> FEATURE:
<223> OTHER INFORMATION: synthetic peptide

<400> SEQUENCE: 19

Gln Asp Met Arg Met Asn
1               5

<210> SEQ ID NO 20
<211> LENGTH: 6
<212> TYPE: PRT
<213> ORGANISM: artificial sequence
<220> FEATURE:
<223> OTHER INFORMATION: synthetic peptide

<400> SEQUENCE: 20

Asn Glu Ile Arg Val Gln
1               5

<210> SEQ ID NO 21
<211> LENGTH: 6
<212> TYPE: PRT
<213> ORGANISM: artificial sequence
<220> FEATURE:
<223> OTHER INFORMATION: synthetic peptide

<400> SEQUENCE: 21

Gln Asp Met Lys Met Asn
1               5

<210> SEQ ID NO 22
<211> LENGTH: 7
<212> TYPE: PRT
<213> ORGANISM: artificial sequence
<220> FEATURE:
<223> OTHER INFORMATION: synthetic peptide

<400> SEQUENCE: 22

Pro Gln Glu Met Arg Met Gln
1               5
```

```
<210> SEQ ID NO 23
<211> LENGTH: 8
<212> TYPE: PRT
<213> ORGANISM: artificial sequence
<220> FEATURE:
<223> OTHER INFORMATION: synthetic peptide

<400> SEQUENCE: 23

Gln Glu Met Arg Met Gln Val Tyr
1               5

<210> SEQ ID NO 24
<211> LENGTH: 8
<212> TYPE: PRT
<213> ORGANISM: artificial sequence
<220> FEATURE:
<223> OTHER INFORMATION: synthetic peptide

<400> SEQUENCE: 24

Ser Gln Glu Met Arg Met Gln Thr
1               5

<210> SEQ ID NO 25
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: Xaa
<222> LOCATION: (1)..(1)
<223> OTHER INFORMATION: no amino acid or any amino acid
<220> FEATURE:
<221> NAME/KEY: MISC_FEATURE
<222> LOCATION: (1)..(1)
<223> OTHER INFORMATION: when present, the amino acid at position 1 can
      be modified by substituent R1
<220> FEATURE:
<221> NAME/KEY: Xaa
<222> LOCATION: (2)..(2)
<223> OTHER INFORMATION: no amino acid or any amino acid
<220> FEATURE:
<221> NAME/KEY: MISC_FEATURE
<222> LOCATION: (2)..(2)
<223> OTHER INFORMATION: when the amino acid at position 1 is not
      present, the amino acid at position 2 can be modified by
      substituent R1
<220> FEATURE:
<221> NAME/KEY: Xaa
<222> LOCATION: (3)..(3)
<223> OTHER INFORMATION: Gln, Glu, Asp or Asn
<220> FEATURE:
<221> NAME/KEY: MISC_FEATURE
<222> LOCATION: (3)..(3)
<223> OTHER INFORMATION: when the amino acids at positions 1 and 2 are
      not present, the amino acid at position 3 can be modified by
      substituent R1
<220> FEATURE:
<221> NAME/KEY: Xaa
<222> LOCATION: (4)..(4)
<223> OTHER INFORMATION: Gln, Glu or Asp
<220> FEATURE:
<221> NAME/KEY: Xaa
<222> LOCATION: (5)..(5)
<223> OTHER INFORMATION: Met, Ile or Leu
<220> FEATURE:
<221> NAME/KEY: Xaa
<222> LOCATION: (6)..(6)
<223> OTHER INFORMATION: Arg, Lys or Orn
<220> FEATURE:
<221> NAME/KEY: Xaa
<222> LOCATION: (7)..(7)
<223> OTHER INFORMATION: Met, Leu, Ile or Val
<220> FEATURE:
<221> NAME/KEY: Xaa
```

```
<222> LOCATION: (8)..(8)
<223> OTHER INFORMATION: Gln, Asn or Glu
<220> FEATURE:
<221> NAME/KEY: MISC_FEATURE
<222> LOCATION: (8)..(8)
<223> OTHER INFORMATION: when the amino acids at positions 9 and 10 are
      not present, the amino acid at position 8 can be modified by
      substituent R2
<220> FEATURE:
<221> NAME/KEY: Xaa
<222> LOCATION: (9)..(9)
<223> OTHER INFORMATION: no amino acid or any amino acid
<220> FEATURE:
<221> NAME/KEY: MISC_FEATURE
<222> LOCATION: (9)..(9)
<223> OTHER INFORMATION: when the amino acid at position 10 is not
      present, teh amino acid at position 9 can be modified by
      substituent R2
<220> FEATURE:
<221> NAME/KEY: MISC_FEATURE
<222> LOCATION: (9)..(9)
<223> OTHER INFORMATION: when the amino acid at position 10 is not
      present, the amino acid at position 9 can be modified by
      substituent R2
<220> FEATURE:
<221> NAME/KEY: Xaa
<222> LOCATION: (10)..(10)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: when present, the amino acid at position 10
      can be modified by subsituent R2

<400> SEQUENCE: 25

Xaa Xaa Xaa Xaa Xaa Xaa Xaa Xaa Xaa Xaa
1               5                   10

<210> SEQ ID NO 26
<211> LENGTH: 7
<212> TYPE: PRT
<213> ORGANISM: artificial sequence
<220> FEATURE:
<223> OTHER INFORMATION: synthetic peptide

<400> SEQUENCE: 26

Gln Glu Met Arg Met Gln Tyr
1               5

<210> SEQ ID NO 27
<211> LENGTH: 7
<212> TYPE: PRT
<213> ORGANISM: artificial sequence
<220> FEATURE:
<223> OTHER INFORMATION: synthetic peptide

<400> SEQUENCE: 27

Gln Glu Met Arg Met Gln Thr
1               5

<210> SEQ ID NO 28
<211> LENGTH: 8
<212> TYPE: PRT
<213> ORGANISM: artificial sequence
<220> FEATURE:
<223> OTHER INFORMATION: synthetic peptide

<400> SEQUENCE: 28

Pro Val Gln Glu Met Arg Met Gln
1               5
```

```
<210> SEQ ID NO 29
<211> LENGTH: 8
<212> TYPE: PRT
<213> ORGANISM: artificial sequence
<220> FEATURE:
<223> OTHER INFORMATION: synthetic peptide

<400> SEQUENCE: 29

Gln Glu Met Arg Met Gln Val Tyr
1               5

<210> SEQ ID NO 30
<211> LENGTH: 6
<212> TYPE: PRT
<213> ORGANISM: artificial sequence
<220> FEATURE:
<223> OTHER INFORMATION: synthetic peptide

<400> SEQUENCE: 30

Asn Glu Met Arg Met Gln
1               5

<210> SEQ ID NO 31
<211> LENGTH: 6
<212> TYPE: PRT
<213> ORGANISM: artificial sequence
<220> FEATURE:
<223> OTHER INFORMATION: synthetic peptide

<400> SEQUENCE: 31

Gln Glu Met Arg Leu Gln
1               5

<210> SEQ ID NO 32
<211> LENGTH: 6
<212> TYPE: PRT
<213> ORGANISM: artificial sequence
<220> FEATURE:
<223> OTHER INFORMATION: synthetic peptide

<400> SEQUENCE: 32

Gln Glu Met Arg Met Asn
1               5

<210> SEQ ID NO 33
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: Xaa
<222> LOCATION: (1)..(1)
<223> OTHER INFORMATION: Gln, Glu, Asp or Asn
<220> FEATURE:
<221> NAME/KEY: Xaa
<222> LOCATION: (2)..(2)
<223> OTHER INFORMATION: Gln, Glu or Asp
<220> FEATURE:
<221> NAME/KEY: Xaa
<222> LOCATION: (3)..(3)
<223> OTHER INFORMATION: Met, Ile or Leu
<220> FEATURE:
<221> NAME/KEY: Xaa
<222> LOCATION: (4)..(4)
<223> OTHER INFORMATION: Arg, Lys or Orn
<220> FEATURE:
<221> NAME/KEY: Xaa
<222> LOCATION: (5)..(5)
<223> OTHER INFORMATION: Met, Leu, Ile or Val
<220> FEATURE:
```

```
<221> NAME/KEY: Xaa
<222> LOCATION: (6)..(6)
<223> OTHER INFORMATION: Gln, Asn or Glu

<400> SEQUENCE: 33

Xaa Xaa Xaa Xaa Xaa Xaa
1               5

<210> SEQ ID NO 34
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: Xaa
<222> LOCATION: (1)..(1)
<223> OTHER INFORMATION: no amino acid or any amino acid
<220> FEATURE:
<221> NAME/KEY: MISC_FEATURE
<222> LOCATION: (1)..(1)
<223> OTHER INFORMATION: when present, the amino acid at position 1 can
      be modified by subsituent R1
<220> FEATURE:
<221> NAME/KEY: Xaa
<222> LOCATION: (2)..(2)
<223> OTHER INFORMATION: no amino acid or any amino acid
<220> FEATURE:
<221> NAME/KEY: MISC_FEATURE
<222> LOCATION: (2)..(2)
<223> OTHER INFORMATION: when the amino acid at position 1 is not
      present, the amino acid at position 2 can be modified by
      subsituent R1
<220> FEATURE:
<221> NAME/KEY: Xaa
<222> LOCATION: (9)..(9)
<223> OTHER INFORMATION: no amino acid or any amino acid
<220> FEATURE:
<221> NAME/KEY: MISC_FEATURE
<222> LOCATION: (9)..(9)
<223> OTHER INFORMATION: when the amino acid at position 10 is not
      present, the amino acid at position 9 can be modified by
      subsituent R2
<220> FEATURE:
<221> NAME/KEY: Xaa
<222> LOCATION: (10)..(10)
<223> OTHER INFORMATION: no amino acid or any amino acid
<220> FEATURE:
<221> NAME/KEY: MISC_FEATURE
<222> LOCATION: (10)..(10)
<223> OTHER INFORMATION: when present, the amino acid at position 10
      can be modified by subsituent R2

<400> SEQUENCE: 34

Xaa Xaa Gln Glu Met Arg Met Gln Xaa Xaa
1               5                   10
```

COMPOUNDS USEFUL IN THE TREATMENT AND/OR CARE OF THE SKIN, HAIR, NAILS, AND/OR MUCOUS MEMBRANES

This application claims the benefit of International Application PCT/US2016/065568, filed Dec. 8, 2016, and EP 15382614.4, filed Dec. 10, 2015, from which the PCT application claims priority, the disclosures of each of which being incorporated herein by reference in their entireties.

FIELD OF THE INVENTION

This invention relates to compounds useful in the treatment and/or care of the skin, hair, nails and/or mucous membranes, compositions containing the compounds and to the use of the compounds. The compounds are useful as skin anti-aging agents and, in particular, as skin rejuvenating agents.

BACKGROUND OF THE INVENTION

The structural stability as well as the physiological function of the skin is affected by aging. With age the turnover of the epidermis is reduced, making it thinner, more fragile, drier and prone to wrinkles. The aging of skin is characterised by a progressive decline in skin thickness and cumulative changes in both the epridermis and dermis that are expressed as wrinkles; loose dry and rough skin; cell proliferation and structural abnormalities; irregular pigmentation; dilated blood vessels; and the degeneration of elastic fiber. Further, with age comes the loss of subcutaneous fat in some parts of the body, which provides a supportive function in the skin. The aging of skin exerts direct effects on both the physical and psychological health and also the social well being of an individual.

The epidermis is the outermost layer of the skin, and protects the body from the environment. Keratinocytes are the main component of the epidermis. The epidermis itself is made up of sublayers that work together to continually rebuild the surface of the skin. The basal layer is the innermost layer of the epidermis and comprises an inner layer of proliferative cells adhered to an underlying basement membrane rich in ECM (extracellular matrix) and growth factors. These basal keratinocyte include a pool of stem cells which have the capacity to both self-perpetuate (self-renew) and also give rise to differentiating cells that constitute one or more tissues. In the latter case, periodically basal cells withdraw from the cell cycle, commit to differentiate terminally, move outward and are eventually shed from the skin surface. Basal cells express several characteristic markers including keratins and transcription factors. Fuchs E., "Skin stem cells: rising to the surface," J. Cell Biol., 180(2):273-284 (Jan. 28, 2008).

One of the effects of the aging process is that the depletion of the pool of stem/progenitor cells (such as basal cells in the epidermis) in the human body. It has been suggested that dysfunction or loss of certain skin resident stem/progenitor cells in chronologically intrinsic or in premature aging skin may result in an impaired regeneration process, reduced wound healing and the development of diverse skin disorders such as an increased susceptibility to injury and infection, epidermal dehydration, wrinkles, pigmentary alterations, hair greying and loss and an increased risk of skin epithelial cancers and melanoma. It has been proposed that the in vivo stimulation of endogenous skin progenitors or the use of ex vivo expanded adult stem/progenitor cells or their progeny represent promising stategies for the juvenescence of aged skin. Dermal mulitpotent cells (DMSCs) and other stem cells have proven to be effective in preventing skin aging by increasing collagen type I and dermal thickness, Furthermore, human induced pluripotent stem cells (hiPSCs) have already been highlighted in developing cell based therapy for intractable disorders, including cardiovascular pathologies, neurogenerative diseases, metabolic conditions and and haemopoitic disorders. It is thought that hiPSCs also hold great promise in skin pathophysiology and regeneration. Peng, Y., et al., "Stem Cells and aberrant signaling of molecular systems in skin aging," Aging Res. Rev. Jan. 19, 2015; pp. 8-21.

The self renewal and pluripotency properties of embyonic stem cells (ESCs) are regulated by an array of protein-coding genes, such as transcription factors and chromatin remodelling enzymes, in a core regulatory circuitry. This circuitry includes the transcription factors OCT4, SOX2 and KLF4, which form self regulatory networks and control a wide range of downstream genes. Extensive studies have indicated that OCT4, SOX2 and KLF4 are required for ESC self-renewal and pluripotency. The over expression of OCT4, SOX2 and KLF4, along with others, can reprogram or dedifferentiate somatic cells into induced pluripotent stem cells (iPSCs) in both mice and human. The dedifferentiation process is the progression from a more to a less differentiated state of the cells. Xu, N., et al., "Micro RNA-145 regulates OCT4, SOX2 and KLF4 and represses pluripotency in human embryonic stem cells," Cell, May 15, 2009; 137(4):647-658. (Xu, et al.)

Recent reports show that differentiation of somatic stem cells and mouse ESCs can be modulated by microRNAs (miRNAs) through posttranscriptional attenuation of key ESC factors. miRNAs are posttranscriptional modulators of gene expression and play an important role in many developmental processes. miRNAs bind to partially complementary target sites in messenger RNA (mRNA) untranslated regions (UTRs), which results in degradation of the target mRNAs, or translational repression of the encoded proteins. miRNAs are thought to have an important role during the process of renewal and differentiation of kerinatocytes (Xu, et al.). In human ESC a specific miRNA plays a key regulator role by direct targeting of the pluripotency factors OCT4, SOX2 and KLF4. The endogenous levels of OCT4, SOX2 and KLF4 are controlled post transcriptionally by miRNA145 in human ESCs. Contrary to the decrease of the pluripotency factors during differentiation, miRNA145 level was relatively low in human ESC and increased during differentiation. miRNA145 is necessary and sufficient to modulate the differentiation progression throught the OCT4/SOX2 pathway. It is known that there is a direct link between an miRNA and the core pluripotency factors OCT4. SOX2 and KLF4 and it has been demonstrated that miRNA145 represses pluripotency and controls ESC differentiation (Xu, et al.).

miRNA145 plays an important role in human stem cell growth and in the differentiation process. miRNA145 is often decreased in human cancers and has been proposed as a tumor suppressor. While there is agreement that miRNA145 levels are low in proliferating cells and increased in non-proliferating cells, there is some controversy on the relationship between the expression of miRNA and growth arrest, differentiation or apoptosis (all three conditions result in inhibition of cell proliferation). The distinction is especially challenging between growth arrest and differentiation, two processes that are often related. It has been shown that: 1) miRNA145 increases in cells induced to differentiate; 2) the time course of miRNA145 increases suggests that at least in some instances, miRNA145 levels could be a late event in the process of differentiation; 3) miRNA145 levels increase in confluent or contact-inhibited cells in the absence of an evidence of differentiation or apoptosis, confirming that growth arrest per se is sufficient to increase miRNA145 expression. miRNA145 levels increase in differentiating cells and also in growth-arrested cells, even in the absence of differentiation. Increased expression during differentiation sometimes occurs as a late event, suggesting that miRNA145 could be required either early or late during the differentiation process. La Rocca, G., "Regulation of microRNA-145 by growth arrest and differentiation," Exp. Cell Res., Feb. 15, 2011; 317(4); 488-95.

Recently the expression of human skin miRNAs and their regulation during keratinocyte differentiation in vitro and in vivo has been studied. The expression patterns of 377 miRNAs during calcium-induced differentiation of primary induced keratinocytes (HKs) in vitro was compared with miRNA expression profiles of epidermal stem cells and transient amplifying and terminally differentiated keratinoctytes isolated from human skin to analyze changes in miRNA expression during keratinocyte differentiation in vivo. The assays suggest that multiple miRNAs cooperate to regulate gene expression in HKs. Hildebrand, J., et al., "A comprehensive analysis of microRNA expression during keratinocyte differentiation in vitro and in vivo," J. Invest. Dermatol. January 2011; 131 91: 20-9.

One of the classical examples for carefully differentiated-specific expression is the expression of keratin proteins. Keratin K5 and keratin K14 form the primary keratin pair of the keratinocytes of stratified squamous epithelia, including the epidermis. They are strongly expressed in the undifferentiated basal cell layer containing the stem cells that are down-regulated in the differentiating suprabasal cell layers. On the other hand, K1 and K10 can be regarded as "keratinization markers" of keratinocytes. In the epidermis, the transition of keratinocytes from the proliferative basal cell layer to the postmitotic suprabasal spinous cell layers in the process of terminal differentiation and keratinization is characterized by a profound change in keratin expression. This involves a switch from expression of the basal cell keratins (K5, K14, K15) to the suprabasal epidermal keratins, keratin K1 and subsequently keratin K10. Moll R, et al., "The human keratins: biology and pathology," Histochem. Cell Biol., June 2008, 129 60; 705-33.

MYC, another factor implicated with the dedifferentiation process, strongly promotes cell proliferation and has been documented as a frequent event in a wide variety of human cancers. Many studies have demonstrated that MYC plays a positive role in keratinocyte proliferation (knockdown of the gene can inhibit keratinocyte proliferation). In addition to its role in cancer, it is also critically involved with many essential cellular processes. Many genes are directly regulated by MYC, including genes that play key roles in metabolism, ribosome biogenesis, cell cycle, apoptosis, differentiation and stem cell maintenance. Watt, F. M., et al., "MYC in mammalian epidermis: how can an oncogene stimulate differentiation?" Nat. Rev. Cancer, 8(3); 234-42 (March 2008); Hofmann J. W., et al., "Reduced expression of MYC increases longevity and enhances health span," Cell 2015, 160(3) 477-88 (January 2015). While age does not have a significant effect on MYCc expression in any mouse tissue examined, many of the biological processes regulated by MYC have also been implicated in aging and age-associated diseases. Reduced expression of MYC increases lifespan in mice and benefits multiple aspects related to the aging process without apparent developmental tradeoffs or changes in stress management pathways. Hofmann, J. W., et al, "Reduced expression of MYC increases longevity and enhances health span," Cell 2015 160(3) 477-88 (January 2015).

Hypertrophic scarring of the skin is caused by excessive activity of skin myofibroblasts after wound healing and often leads to functional and/or aesthetic disturbance with significant impairment of the patient's quality of life. In physiologic wound healing, progenitor cells such as fibroblasts are activated and differentiate to myofibroblasts (essentials in the wound closure process: they migrate to the defect where they synthesize and deposit extracellular matrix components and mediate wound contraction). One of the major growth factors driving fibroblast differentiation and maturation to myofibroblasts has been shown to be transforming growth factor beta 1 (TGF-β1), which is present at high concentrations in wound granulation tissue. TGF-β1 coordinately induces the expression of collagen type I and α-smooth muscle actin (α-SMA), a myofibroblast marker. miRNA-based treatments have been recently proposed for the treatment of pathological scarring. A recent study showed an increase of miR-145 levels in skin hypertrophic scar tissue and also in TGF-β1-induced skin myofibroblasts compared to healthy skin. The data demonstrates that TGF-β1 induces miR-145 expression in fibroblasts upregulating α-SMA expression. Furthermore, treatment of myofibroblasts with a miR-145 inhibitor strongly decreased their alpha-1 type I collagen expression, TGF-β1 secretion, contractile force generation, and migration. The inhibition of miR-145 significantly reduces skin myofibroblast activity and this effect suggesting miR-145 has a therapeutic target to prevent or reduce hypertrophic scarring of the skin. Gras, C., et al., "miR-145 Contributes to Hypertrophic Scarring of the Skin by Inducing Myofibroblast Activity," Mol Med. 21:296-304 (Apr. 9, 2015).

Host defense against microbial invasion involves appropriate innate immune response initiated by innate receptors that can sense the invading pathogens. IL-10 plays a crucial role in preventing inflammatory pathologies and maintaining host homeostasis. During an infection, the absence of IL-10 can be accompanied with immunopathological tissue damage that is detrimental to the host, whereas excessive amount of IL-10 always results in chronic infectious diseases caused by less clearance of pathogens. Innate immune responses must be tightly regulated to avoid overactivation and subsequent inflammatory damage to host tissue while eliminating invading pathogens. Besides providing a structural barrier, the skin contains several immune cells that can be activated by invading pathogens or skin damage. One of the most important immune cells involved in wound healing is the macrophage, which exhibits different immunological functions in the skin, including phagocytosis and antigen-presentation. Furthermore, macrophages produce many cytokines and chemokines that stimulate new capillary growth, collagen synthesis and fibrosis. This immune cell is thought to orchestrate the wound healing process throughout the different phases. IL-10 is a crucial suppressor of inflammatory responses and its expression is under precise regulation involving complex regulatory networks and multiple feedback loops. MicroRNAs are now emerging as critical regulators in immune response. miR-145, downregulated by type I IFN (IFN-I), promotes innate IL-10 expression in macrophages by Toll-like receptor (TLR) signals, that creates precise coordination of innate immune responses. Lin, L., et al., "Type I IFN inhibits innate IL-10 production in macrophages by downregulating microRNA-145," J. Immunol., 191(7):3896-904 (October 2013)/

Melanins are complex pigments that provide the skin, hair and eyes of mammals with color and photoprotection against ionizing radiation. Melanogenesis is physiological process resulting of the synthesis of the melanin pigments, and is characterized, in summary, by the production process and subsequent distribution of melanin by melanocytes. After the production, melanin, within the melanosomes (lysosome-related organelles which have the unique capacity to produce melanin pigment and which progress through four sequential morphological steps as they mature, is transferred to the adjacent keratinocytes through the dendrites present in the melanocytes, where it shall be transported and degraded. Skin pigmentation depends on the number, the chemical nature of melanin and content (the tyrosinase activity), and distribution of melanosomes produced, and transferred by each melanocyte to a cluster of keratinocytes surrounding it. miRNA-based treatments may offer an alternative to current treatments for modification of the skin color by specifically targeting key genes in melanogenesis (synthesis of melanin by melanocytes). Some miRNAs have been identified as regulators of the melanogenesis. In this sense, downregulation of miR-145 in a melanocyte cell model revealed increased expression of melanogenesis genes (Sox9, Mitf, Tyr, Trp1, Myo5a, Rab27a, and Fscn1). Dynoodt, P., et al., "Identification of miR-145 as a key regulator of the pigmentary process," J. Invest. Dermatol., 133(1):201-9 (January 2013).

In the skin, the adipocytes are located in the deepest layers of the dermis, the hypodermis. The main function of the adipocytes is the storage of fat in vacuoles in the form of triglycerides. Nutrients providing excess calories are converted to triacylglycerol (TAG) for storage in lipid droplets of white adipose tissue (WAT). The content of TAG in WAT is determined by the balance of anabolic (esterification of glycerol with fatty acids) and catabolic (lipolytic reactions that hydrolyze TAG to glycerol and fatty acids, referred to as lipolysis) pathways. In addition to this energy-related function, these cells are also involved in the production of some hormones (estrogen) as well as in the synthesis of molecules implicated in inflammatory response. MicroRNAs (miRNAs) have multiple effects in adipose tissue. miR-145 is also present in human adipose tissue in fat cells and regulates adipocyte lipolysis via multiple mechanisms. Lorente-Cebrián. S., et al., "MicroRNAs regulate human adipocyte lipolysis: effects of miR-145 are linked to TNF-α," PLoS One.; 9(1):e86800 (Jan. 24 2014); Lin, Y. Y., "KSRP and MicroRNA 145 are negative regulators of lipolysis in white adipose tissue," Mol. Cell Biol., 34(12): 2339-49 (June 2014).

There is a need to provide a compound that can alleviate, prevent or delay the aging of the skin or the symptoms of aging of the skin. There is a need to provide a compound that can act to rejuvenate the skin. There is a need to provide a compound that promotes cell renewal/regeneration in the skin. There is a need to provide a compound that is active in increasing the level of transcription factors that promote cell renewal (dedifferention) in the skin and that can recover the germinative power of keratinocytes in the skin. There is a need to provide a compound that is active in reducing miRNA expression in human keratinocytes.

There is a need to provide a compound that can treat hypertrophic scarring of the skin. There is a need to provide a compound that can promote wound healing.

The present invention sets out to solve all or some of the above-identified problems and meet some or all of the above-identified needs.

SUMMARY OF THE INVENTION

In a first aspect, the invention provides a compound of general formula (I):

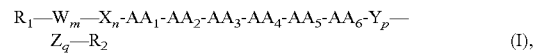

$$R_1-W_m-X_n-AA_1-AA_2-AA_3-AA_4-AA_5-AA_6-Y_p-Z_q-R_2 \quad (I),$$

its stereoisomers and/or its cosmetically or pharmaceutically acceptable salts, wherein:

$AA_1$ is selected from the group consisting of Gln, Glu, Asp and Asn;

$AA_2$ is selected from the group consisting of Glu, Gln and Asp;

$AA_3$ is selected from the group consisting of Met, Ile and Leu;

$AA_4$ is selected from the group consisting of Arg, Lys and Orn;

$AA_5$ is selected from the group consisting of Met, Leu, Ile and Val;

$AA_6$ is selected from the group consisting of Gln, Asn and Glu;

W, X, Y and Z are each independently an amino acid;

m, n, p and q are each independently 0 or 1;

$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ or $R_2$ are not α-amino acids, with the proviso that the compound is not Ac-Asn-Glu-Met-Arg-Met-Gln-OH (Ac-[SEQ ID.30]-OH), Ac-Gln-Glu-Met-Arg-Leu-Gln-OH (Ac-[SEQ ID.31]—OH), or Palm-Gln-Glu-Met-Arg-Met-Asn-OH (Palm-[SEQ ID.32]-OH).

It has been found that compounds of general formula (I) can decrease miRNA expression in human keratinocytes and, as a result, increase the levels of transcription factors involved in the self-renewing processes of the skin. The effect is a recovery of the self-renewing properties of basal keratinocytes (in the skin) and skin rejuvenation. Further, the compounds are useful in the treatment or prevention of the symptoms of aging in the skin, the treatment of hypertrophic scarring and the treatment of wound healing in the skin.

In a second aspect, the invention provides a cosmetic or pharmaceutical composition comprising a compound according to general formula (I), its stereoisomers and/or its cosmetically or pharmaceutically acceptable salts, together with at least one cosmetically or pharmaceutically acceptable excipient or adjuvant.

In a third aspect, the invention provides the use of a compound of the invention, its stereoisomers and/or its pharmaceutically acceptable salts or a pharmaceutical composition comprising the compound, its stereoisomers and/or its pharmaceutically acceptable salts for the cosmetic, non-therapeutic treatment and/or care of the skin, hair, nails and/or mucous membranes.

In a fourth aspect, the invention provides a compound of the invention, its stereoisomers and/or its pharmaceutically acceptable salts or a pharmaceutical composition comprising the compound, its stereoisomers and/or its pharmaceutically acceptable salts for use as a medicament.

In a fifth aspect, the invention provides a cosmetic, non-therapeutic method of treating the skin, hair, nail and/or mucous membranes in a subject comprising administering a cosmetically effective amount of a compound of the invention or a pharmaceutical composition comprising the compound, to the subject.

In a sixth aspect, the invention provides a method of treating or preventing a disease or disorder in a subject comprising administering a therapeutically effective amount of a compound of the invention or a pharmaceutical composition comprising the compound, to the subject.

DESCRIPTION OF THE INVENTION

The embodiments as set out below are applicable to all of the above-mentioned aspects of the invention.

Definitions

In order to facilitate the comprehension of this invention, the meanings of some terms and expressions as they are used in the context of the invention are included.

In the context of this invention "skin" is understood to be the layers which comprise it, from the uppermost layer or stratum corneum to the lowermost layer or hypodermis, both inclusive. These layers are composed of different types of cells such as keratinocytes, fibroblasts, melanocytes, mast cells, neurones and/or adipocytes among others. The term "skin" also comprises the scalp. The term "skin" includes the skin of mammals and includes human skin.

The term "treatment", according to its use in the context of this specification when it is not accompanied by the qualifications "cosmetic, non-therapeutic", means the administration of a compound according to the invention to alleviate or eliminate a disease or disorder or reduce or eliminate one or more symptoms associated with said disease or disorder. The term "treatment" also covers alleviating or eliminating physiological consequences of the disease or disorder.

When the terms "treatment" and "care" are accompanied by the qualifications "cosmetic" and/or "non-therapeutic", it means that the treatment or care is such and, for example, has the aim of improving the aesthetic appearance of the skin, hair, nails and/or mucous membranes. In particular, the treatment or care can have the the aim of improving cosmetic properties of the skin, hair and/or mucous membranes such as, for example and not restricted to, the level of hydration, elasticity, firmness, shine, tone or texture, among others. The term "care" in the context of this specification refers to the maintenance of the qualities of the skin, hair and/or mucous membranes. Said qualities are subject to being improved or maintained by cosmetic treatment and/or care of the skin, hair and/or mucous membranes both in healthy subjects as well as in those which present diseases and/or disorders of the skin and/or mucous membranes such as, for example and not restricted to, ulcers and injuries to skin, psoriasis, dermatitis, acne or rosacea, among others.

The term "prevention", as used in this invention, refers to the ability of a compound of the invention to prevent, delay or hinder the appearance or development of a disease or disorder, or to prevent, delay or hinder the change in a cosmetic property of the skin, mucous membranes and/or hair.

In the context of this invention, the term "aging" refers to the changes experienced by the skin with age (chronoaging) or through exposure to the sun (photoaging) or to environmental agents such as tobacco smoke, extreme climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange-peel skin, loss of collagen structure and other histological changes of the stratum corneum, of the dermis, epidermis, vascular system (for example the appearance of spider veins or telangiectasia) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of various environmental factors such as exposure to tobacco smoke, exposure to pollution, and climatic conditions such as cold and/or wind also contribute to the aging of the skin.

In this description the abbreviations used for amino acids follow the rules of IUPAC-IUB Commission of Biochemical Nomenclature specified in *Eur. J. Biochem.*, (1984), 138, 9-37.

Thus, for example, Gly represents $NH_2$—$CH_2$—COOH, Gly- represents $NH_2$—$CH_2$—CO—, -Gly represents —NH—$CH_2$—COOH and -Gly- represents —NH—$CH_2$—CO—. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

| Name/Symbol | Residue |
|---|---|
| Asparagyl-Asn-N | (structure of asparagine residue) |
| Glutaminyl-Gln-Q | (structure of glutamine residue) |
| Histidyl-His-H | (structure of histidine residue) |
| Glycyl-Gly-G | (structure of glycine residue) |
| Lysyl-Lys-K | (structure of lysine residue) |
| Tyrosyl-Tyr-Y | (structure of tyrosine residue) |
| Leucyl-Leu-L | (structure of leucine residue) |

TABLE 1-continued

| Name/Symbol | Residue |
|---|---|
| Aspartyl-Asp-D | (structure of aspartate residue) |
| Glutamyl-Glu-E | (structure of glutamate residue) |
| Isoleucyl-Ile-I | (structure of isoleucine residue) |
| Valyl-Val-V | (structure of valine residue) |
| Methionyl-Met-M | (structure of methionine residue) |
| Tryptophyl-Trp-W | (structure of tryptophan residue) |
| Ornithyl-Orn- | (structure of ornithine residue) |

TABLE 1-continued

| Name/Symbol | Residue |
|---|---|
| Diaminobutyryl-Dbu- | (structure) |
| Diaminopropionyl-Dpr- | (structure) |
| 4-Aminobenzoyl-4-Abz- | (structure) |
| Citrullyl-Cit- | (structure) |
| Threonyl-Thr-T | (structure) |
| Arginyl-Arg-R | (structure) |
| Leucyl-Leu-L | (structure) |

The abbreviation "Ac—" is used in this description to designate the acetyl group ($CH_3$—CO—), the abbreviation "Palm-" is used to designate the palmitoyl group ($CH_3$—$(CH_2)_{14}$—CO—) and the abbreviation "Myr-" is used to designate the myristoyl group ($CH_3$—$(CH_2)_{12}$—CO—).

The term "non-cyclic aliphatic group" is used in this invention to cover the linear or branched alkyl, alkenyl and alkynyl groups.

The term "alkyl group" refers to a linear or branched saturated group, which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a single bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a single bond, including, for example and not restricted to, the vinyl (—$CH_2$=$CH_2$), allyl (—$CH_2$—CH=$CH_2$), prenyl, oleyl, linoleyl groups and similar.

The term "alkynyl group" refers to a linear or branched group, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the ethynyl group, 1-propynyl, 2-propynyl, 1-butynyl, 2-butynyl, 3-butynyl, pentynyl, such as 1-pentynyl, and similar. The alkynyl groups can also contain one or more double carbon-carbon bonds, including, for example and not restricted to, the but-1-en-3-ynyl, pent-4-en-1-ynyl groups and similar.

The term "alicyclic group" is used in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and which is bound to the rest of the molecule by a single bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, which is bound to the rest of the molecule by a single bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, which is bound to the rest of the molecule by a single bond, including, for example and not restricted to, the cyclooct-2-yn-1-yl group and similar. Cycloalkynyl groups can also contain one or more double carbon-carbon bonds, including, for example and not restricted to, the cyclooct-4-en-2-ynyl group and similar.

The term "aryl group" refers to an aromatic group which has between 6 and 30, preferably between 6 and 18, more preferably between 6 and 10, yet more preferably 6 or 10 carbon atoms, which comprises 1, 2, 3 or 4 aromatic rings, bound by a carbon-carbon bond or fused, including, for example and not restricted to, phenyl, naphthyl, diphenyl, indenyl, phenanthryl or antranyl among others; or to an aralkyl group.

The term "aralkyl group" refers to an alkyl group substituted by an aromatic group, with between 7 and 24 carbon atoms and including, for example and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—$CH(phenyl)_2$ and similar.

The term "heterocyclyl group" refers to a hydrocarbonated ring or system of rings of 3-10 members, in which one or more of the atoms in the ring or rings, preferably 1, 2 or 3 of the atoms of the ring or rings, is a different element to carbon, such as nitrogen, oxygen or sulfur and it can be saturated or unsaturated. For the purposes of this invention, the heterocycle can be a cyclic, monocyclic, bicyclic or tricyclic system, which may include systems of fused rings; and the nitrogen, carbon or sulfur atoms in the heterocyclyl radical may be optionally oxidized; the nitrogen atom may be optionally quaternized; and the heterocyclyl radical may be partially or completely saturated or be aromatic. The greatest preference is for the term heterocyclyl to refer to a ring of 5 or 6 members. Examples of saturated heterocyclyl groups are dioxane, piperidine, piperazine, pyrrolidine, morpholine and thiomorpholine. Examples of aromatic heterocyclyl groups, also known as heteroaromatic groups are pyridine, pyrrole, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms different to carbon including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As is understood in this technical field, there may be a certain degree of substitution of the aforementioned groups. Therefore, there can be substitution in any of the groups of this invention where it is explicitly stated. The references in this document to substituted groups in the groups of this invention indicate that the specified radical can be substituted in one or more positions available by one or more substitutes, preferably in 1, 2 or 3 positions, more preferably in 1 or 2 positions, yet more preferably in 1 position. These substituents include, for example and not restricted to, alkyl $C_1$-$C_4$, hydroxyl; alkoxyl $C_1$-$C_4$, amino; aminoalkyl $C_1$-$C_4$, carbonyloxyl $C_1$-$C_4$, oxycarbonyl $C_1$-$C_4$, halogen such as fluoride, chlorine, bromine and iodine; cyan; nitro; azide; alkylsulfonyl $C_1$-$C_4$, thiol; alkylthio $C_1$-$C_4$, aryloxy such as phenoxyl; —$NR_b(C=NR_b)NR_bR_c$, wherein $R_b$ and $R_c$ are independently selected from the group consisting of H, alkyl $C_1$-$C_4$, alkenyl $C_2$-$C_4$, alkynyl $C_2$-$C_4$, cycloalkyl $C_3$-$C_{10}$, aryl $C_6$-$C_{18}$, aralkyl $C_7$-$C_{17}$, heterocyclyl of 3-10 members or protective group of the amino group.

COMPOUNDS OF THE INVENTION

A first aspect of the invention relates to a compound of general formula (I):

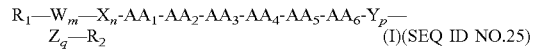
$$Z_q\text{—}R_2 \quad \text{(I)(SEQ ID NO.25)}$$

its stereoisomers and/or its cosmetically or pharmaceutically acceptable salts, wherein:
  $AA_1$ is selected from the group consisting of Gln, Glu, Asp and Asn;
  $AA_2$ is selected from the group consisting of Glu, Gln and Asp;
  $AA_3$ is selected from the group consisting of Met, Ile and Leu;
  $AA_4$ is selected from the group consisting of Arg, Lys and Orn;
  $AA_5$ is selected from the group consisting of Met, Leu, Ile and Val;
  $AA_6$ is selected from the group consisting of Gln, Asn and Glu;
  W, X, Y and Z are each independently an amino acid;
  m, n, p and q are each independently 0 or 1;
  $R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
  $R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
  $R_1$ or $R_2$ are not α-amino acids
with the proviso that the compound is not Ac-Asn-Glu-Met-Arg-Met-Gln-OH (Ac-[SEQ ID.30]-OH), Ac-Gln-Glu-Met-Arg-Leu-Gln-OH (Ac-[SEQ ID.31]-OH), or Palm-Gln-Glu-Met-Arg-Met-Asn-OH (Palm-[SEQ ID.32]-OH).

Groups $R_1$ and $R_2$ are bound to the amino-terminal (N-terminal) and carboxy-terminal (C-terminal) ends of the peptide sequences respectively.

$R_1$ can be selected from the group consisting of H, a polymer derived from polyethylene glycol and $R_5$—CO—, wherein $R_5$ is selected from the group consisting of substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms and $R_5$—CO— is not an α-amino acid. In one embodiment, $R_1$ is selected from the group consisting of H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl myristoyl, palmitoyl, stearoyl, oleoyl and linoleoyl. In one embodiment, $R_1$ is H, acetyl, lauroyl, myristoyl or palmitoyl or $R_1$ is acetyl or palmitoyl.

$R_2$ can be selected from the group consisting of —$NR_3R_4$, —$OR_3$, —$SR_3$, wherein $R_3$ and $R_4$ are independently selected from the group consisting of H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_3R_4$ is not an α-amino acid. Optionally, $R_3$ and $R_4$ can be bound by a saturated or unsaturated carbon-carbon bond, forming a cycle with the nitrogen atom. In one embodiment, $R_2$ is —$NR_3R_4$ or —$OR_3$. In one embodiment, $R_3$ and $R_4$ are independently selected from the group consisting of H, a polymer derived from polyethylene glycol with a molecular weight comprised between 200 and 35000 Daltons, methyl, ethyl, hexyl, dodecyl and hexadecyl or $R_3$ is H and $R_4$ is selected from the group consisting of H, methyl, ethyl, hexyl, dodecyl and hexadecyl. In accordance with one embodiment, $R_2$ is selected from —OH and —$NH_2$.

In accordance with another embodiment of this invention $R_1$ is selected from the group consisting of H, acetyl, lauroyl, myristoyl and palmitoyl, preferably $R_1$ is selected from the group consisting of H, acetyl, myristoyl and palmitoyl and $R_2$ is selected from the group consisting of —OH, —$NH_2$ and —$NHR_3$, wherein $R_3$ is a $C_6$ to $C_{18}$ alkyl group, preferably $R_2$ is selected from the group consisting of —OH, —$NH_2$, and —$NHR_3$ where $R_3$ is a $C_6$ or $C_{16}$ alkyl group. In one embodiment $R_1$ is selected from the group consisting of H, acetyl, myristoyl and palmitoyl and $R_2$ is selected from the group consisting of —OH, —$NH_2$, and —$NHC_6H_{13}$.

In accordance with another particular embodiment, the most preferred structures of the polymer derived from polyethylene glycol are the group (—$CH_2$—$OH_2$—O)$_r$—H in which r is a number comprised between 4 and 795 and the group

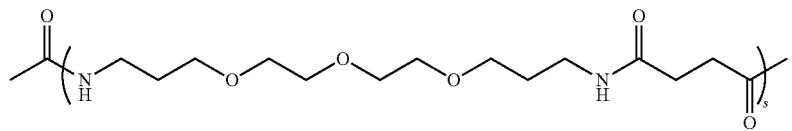

where s is a number comprised between 1 and 125.

In accordance with another embodiment of this invention m, n, p and q are 0. The sequence is then $R_1$-$AA_1$-$AA_2$-$AA_3$-$AA_4$-$AA_5$-$AA_6$-$R_2$ ($R_1$-[SEQ ID NO.33]—$R_2$). In one embodiment the sum of m, n, p and q is 1 or 2.

In one embodiment of the first aspect of the invention,
(i) $AA_1$ is Gln, $AA_2$ is Glu, $AA_3$ is Met, $AA_4$ is Arg, $AA_5$ is Met, and $AA_6$ is Gln, or
(ii) $AA_1$ is Gln, $AA_2$ is Glu, $AA_3$ is Met, $AA_4$ is Arg, $AA_5$ is Met and $AA_6$ is Gln, and 1 to 3 of $AA_1$, $AA_2$, $AA_3$, $AA_4$, $AA_5$ and $AA_6$ are replaced providing that:
when $AA_1$ is replaced, it is replaced by an amino acid selected from the group consisting of Glu, Asp and Asn;
when $AA_2$ is replaced, it is replaced by an amino acid selected from the group consisting of Gln and Asp;
when $AA_3$ is replaced, it is replaced by an amino acid selected from the group consisting of Ile and Leu;
when $AA_4$ is replaced, it is replaced by an amino acid selected from the group consisting of Lys and Orn;
when $AA_5$ is replaced, it is replaced by an amino acid selected from the group consisting of Leu, Ile and Val; and
when $AA_6$ is replaced, it is replaced by an amino acid selected from the group consisting of Asn and Glu.

Thus, in this embodiment of the invention, —$W_m$—$X_n$-$AA_1$-$AA_2$-$AA_3$-$AA_4$-$AA_5$-$AA_6$-$Y_p$—$Z_q$— represents a sequence of 6 to 8 amino acids in which -$AA_1$-$AA_2$-$AA_3$-$AA_4$-$AA_5$-$AA_6$- is -Gln-Glu-Met-Arg-Met-Gln- wherein up to 3 (i.e. 0 to 3) of amino acids $AA_1$ to $AA_6$ are replaced. —$W_m$—$X_n$-Gln-Glu-Met-Arg-Met-Gln-$Y_p$—$Z_q$-(SEQ ID NO.34) represents the sequence when none of $AA_1$ to $AA_6$ is replaced.

In one embodiment of the first aspect of the invention, $AA_1$ is Gln, $AA_2$ is Glu, $AA_3$ is Met, $AA_4$ is Arg, $AA_5$ is Met and $AA_6$ is Gln, and 3 of $AA_1$, $AA_2$, $AA_3$, $AA_4$, $AA_5$ and $AA_6$ are replaced providing that:
when $AA_1$ is replaced, it is replaced by an amino acid selected from the group consisting of Glu, Asp and Asn;
when $AA_2$ is replaced, it is replaced by an amino acid selected from the group consisting of Gln and Asp;
when $AA_3$ is replaced, it is replaced by an amino acid selected from the group consisting of Ile and Leu;
when $AA_4$ is replaced, it is replaced by an amino acid selected from the group consisting of Lys and Orn;
when $AA_5$ is replaced, it is replaced by an amino acid selected from the group consisting of Leu, Ile and Val; and
when $AA_6$ is replaced, it is replaced by an amino acid selected from the group consisting of Asn and Glu.

Thus, in this embodiment of the invention, —$W_m$—$X_n$-$AA_1$-$AA_2$-$AA_3$-$AA_4$-$AA_5$-$AA_6$-$Y_p$—$Z_q$— represents a sequence of 6 to 8 amino acids in which -$AA_1$-$AA_2$-$AA_3$-$AA_4$-$AA_5$-$AA_6$- is -Gln-Glu-Met-Arg-Met-Gln- wherein 3 of amino acids $AA_1$ to $AA_6$ are replaced. In one embodiment, $AA_1$, $AA_3$, and $AA_5$ are replaced. In one embodiment, $AA_1$ is replaced by Asn, $AA_3$ is replaced by Ile, and $AA_5$ is replaced by Val. In one embodiment, $AA_2$, $AA_4$, and $AA_6$ are replaced. In one embodiment, $AA_2$ is replaced by Asp, $AA_4$ is replaced by Lys, and $AA_6$ is replaced by Asn.

In one embodiment of the first aspect of the invention, $AA_1$ is Gln, $AA_2$ is Glu, $AA_3$ is Met, $AA_4$ is Arg, $AA_5$ is Met and $AA_6$ is Gln, and 2 of $AA_1$, $AA_2$, $AA_3$, $AA_4$, $AA_5$ and $AA_6$ are replaced providing that:

when $AA_1$ is replaced, it is replaced by an amino acid selected from the group consisting of Glu, Asp and Asn;
when $AA_2$ is replaced, it is replaced by an amino acid selected from the group consisting of Gln and Asp;
when $AA_3$ is replaced, it is replaced by an amino acid selected from the group consisting of Ile and Leu;
when $AA_4$ is replaced, it is replaced by an amino acid selected from the group consisting of Lys and Orn;
when $AA_5$ is replaced, it is replaced by an amino acid selected from the group consisting of Leu, Ile and Val; and
when $AA_6$ is replaced, it is replaced by an amino acid selected from the group consisting of Asn and Glu.

Thus, in this embodiment of the invention, —$W_m$—$X_n$-$AA_1$-$AA_2$-$AA_3$-$AA_4$-$AA_5$-$AA_6$-$Y_p$—$Z_q$— represents a sequence of 6 to 8 amino acids in which -$AA_1$-$AA_2$-$AA_3$-$AA_4$-$AA_5$-$AA_6$- is -Gln-Glu-Met-Arg-Met-Gln- wherein 2 of amino acids $AA_1$ to $AA_6$ are replaced. In one embodiment, $AA_1$ and $AA_2$ are replaced. In one embodiment $AA_1$ and $AA_2$ are replaced providing that $AA_1$ is replaced by an amino acid selected from the group consisting of Glu and Asp, and $AA_2$ is replaced by Gln. In one embodiment, $AA_4$ and $AA_5$ are replaced. In one embodiment $AA_4$ is replaced by Lys and $AA_5$ is replaced by Leu.

In one embodiment of the first aspect of the invention, $AA_1$ is Gln, $AA_2$ is Glu, $AA_3$ is Met, $AA_4$ is Arg, $AA_5$ is Met and $AA_6$ is Gln, and one of $AA_1$, $AA_2$, $AA_3$, $AA_4$, $AA_5$ and $AA_6$ is replaced providing that:

when $AA_1$ is replaced, it is replaced by an amino acid selected from the group consisting of Glu, Asp and Asn;
when $AA_2$ is replaced, it is replaced by an amino acid selected from the group consisting of Gln and Asp;
when $AA_3$ is replaced, it is replaced by an amino acid selected from the group consisting of Ile and Leu;
when $AA_4$ is replaced, it is replaced by an amino acid selected from the group consisting of Lys and Orn;
when $AA_5$ is replaced, it is replaced by an amino acid selected from the group consisting of Leu, Ile and Val; and
when $AA_6$ is replaced, it is replaced by an amino acid selected from the group consisting of Asn and Glu.

Thus, in this embodiment of the invention, —$W_m$—$X_n$-$AA_1$-$AA_2$-$AA_3$-$AA_4$-$AA_5$-$AA_6$-$Y_p$—$Z_q$— represents a sequence of 6 to 8 amino acids in which -$AA_1$-$AA_2$-$AA_3$-$AA_4$-$AA_5$-$AA_6$- is -Gln-Glu-Met-Arg-Met-Gln- wherein one of amino acids $AA_1$ to $AA_6$ is replaced. In one embodiment, $AA_1$ is replaced. In one embodiment, $AA_2$ is replaced. In one embodiment, $AA_3$ is replaced. In one embodiment, $AA_4$ is replaced. In one embodiment, $AA_5$ is replaced.

In one embodiment of the first aspect of the invention, $AA_1$ is not Asn, $AA_5$ is not Leu and/or $AA_6$ is not Asn.

Compounds of the invention include those containing amino acid sequences selected from the group of sequences outlined in Table 2, in which their sequence identifier is detailed, their stereoisomers, mixtures thereof and/or their cosmetically or pharmaceutically acceptable salts.

TABLE 2

| SEQUENCE | IDENTIFIER |
| --- | --- |
| Gln-Glu-Met-Arg-Met-Gln | SEQ ID NO. 1 |
| Asp-Glu-Met-Arg-Met-Gln | SEQ ID NO. 2 |

TABLE 2-continued

| SEQUENCE | IDENTIFIER |
| --- | --- |
| Glu-Glu-Met-Arg-Met-Gln | SEQ ID NO. 3 |
| Gln-Gln-Met-Arg-Met-Gln | SEQ ID NO. 4 |
| Gln-Glu-Met-Lys-Met-Gln | SEQ ID NO. 5 |
| Gln-Glu-Met-Orn-Met-Gln | SEQ ID NO. 6 |
| Gln-Glu-Met-Arg-Met-Glu | SEQ ID NO. 7 |
| Gln-Glu-Met-Arg-Met-Asn | SEQ ID NO. 8 |
| Glu-Glu-Met-Arg-Met-Gln | SEQ ID NO. 9 |
| Gln-Asp-Met-Arg-Met-Gln | SEQ ID NO. 10 |
| Gln-Glu-Leu-Arg-Met-Gln | SEQ ID NO. 11 |
| Gln-Glu-Ile-Arg-Met-Gln | SEQ ID NO. 12 |
| Gln-Glu-Met-Arg-Ile-Gln | SEQ ID NO. 13 |
| Gln-Glu-Met-Arg-Leu-Gln | SEQ ID NO. 14 |
| Glu-Glu-Ile-Arg-Met-Gln | SEQ ID NO. 15 |
| Asp-Gln-Met-Arg-Met-Gln | SEQ ID NO. 16 |
| Glu-Gln-Met-Arg-Met-Gln | SEQ ID NO. 17 |
| Gln-Glu-Met-Lys-Leu-Gln | SEQ ID NO. 18 |
| Gln-Asp-Met-Arg-Met-Asn | SEQ ID NO. 19 |
| Asn-Glu-Ile-Arg-Val-Gln | SEQ ID NO. 20 |
| Gln-Asp-Met-Lys-Met-Asn | SEQ ID NO. 21 |
| Pro-Gln-Glu-Met-Arg-Met-Gln | SEQ ID NO. 22 |
| Gln-Glu-Met-Arg-Met-Gln-Val-Tyr | SEQ ID NO. 23 |
| Ser-Gln-Glu-Met-Arg-Met-Gln-Thr | SEQ ID NO. 24 |

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that $AA_4$ can be -Lys-, it is understood that AA4 is selected from -L-Lys-, -D-Lys- or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples of non-encoded amino acids are, without restriction, citrulline, ornithine, sarcosine, desmosine, norvaline, 4-aminobutyric acid, 2-aminobutyric acid, 2-aminoisobutyric acid, 6-aminohexanoyc acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "*Unusual amino acids in peptide synthesis*" by D. C. Roberts and F. Vellaccio, in *The Peptides, Vol.* 5 (1983), *Chapter VI*, Gross E. and Meienhofer J., Eds., Academic Press, New York, USA or in the commercial catalogues of the companies specialized in the field.

In the context of this invention, when n, m, p or q are not 0 it is clearly understood that the nature of W, X, Y and/or Z does not hinder the activity of the compounds of the invention, but it contributes to it or has no effect on it. In one embodiment, W, X, Y and Z are each independently selected from the group consisting of Pro, Val, Ser, Tyr and Thr. In one embodiment, W and X are independently selected from the group consisting of Pro, Val and Ser. In one embodiment, Y and Z are independently selected from the group consisting of Val, Tyr and Thr.

The cosmetically or pharmaceutically acceptable salts of the compounds provided within the present invention are also found within the field of this invention. The term "cosmetically or pharmaceutically acceptable salts" means a salt recognized for its use in animals and more specifically in human beings, and includes salts used to form base addition salts, either they are inorganic, for example and not restricted to, lithium, sodium, potassium, calcium, magnesium, manganese, copper, zinc or aluminum among others, or they are organic, for example and not restricted to, ethylamine, diethylamine, ethylenediamine, ethanolamine, diethanolamine, arginine, lysine, histidine or piperazine among others, or acid addition salts, either they are organic, for example and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, for example and not restricted to, chloride, sulfate, borate or carbonate, among others. The nature of the salt is not critical, provided that it is cosmetically or pharmaceutically acceptable. The cosmetically or pharmaceutically acceptable salts of the compounds of the invention can be obtained by the conventional methods, well known in the prior art [Berge, S. M., et al., "*Pharmaceutical Salts*," (1977), *J. Pharm. Sci.*, 66, 1-19].

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as using solid phase peptide synthesis methods [Stewart, J. M., and Young, J. D., "*Solid Phase Peptide Synthesis,* 2nd edition," (1984), Pierce Chemical Company, Rockford, Ill.; Bodanzsky, M., and Bodanzsky, A., "*The practice of Peptide Synthesis,*" (1994), Springer Verlag, Berlin; Lloyd-Williams, P., et al., "*Chemical Approaches to the Synthesis of Peptides and Proteins,*" (1997), CRC, Boca Raton, Fla., USA], synthesis in solution, enzymatic synthesis [Kullmann, W, "*Proteases as catalysts for enzymic syntheses of opioid peptides,*" (1980), *J. Biol. Chem.,* 255(17), 8234-8238] or any combination thereof. The compounds can also be obtained by fermentation of a bacterial strain, modified or unmodified, by genetic engineering with the objective of producing the desired sequences, or by controlled hydrolysis of proteins with animal or plant origins, preferably plant, which free peptide fragments that contain, at least, the desired sequence.

For example, a method of obtaining the compounds (I) of the invention, their stereoisomers and mixtures thereof comprises the stages of:
coupling of an amino acid, with the N-terminal end protected and the C-terminal end free, with an amino acid with the N-terminal end free and the C-terminal end protected or bound to a solid support;
elimination of the protective group of the N-terminal end; repetition of the coupling sequence and elimination of the protective group of the N-terminal end until the desired peptide sequence is obtained;
elimination of the protective group of the C-terminal end or cleavage of the solid support.

Preferably, the C-terminal end is bound to a solid support and the process is carried out in solid phase and, therefore, comprises the coupling of an amino acid with the N-terminal end protected and the C-terminal end free with an amino acid with the N-terminal end free and the C-terminal end bound to a polymeric support; elimination of the protective group of the N-terminal end; and repetition of this sequence as many times as is necessary to thus obtain the compound of the desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or an amino acid previously bound to the polymeric support. Convergent synthesis strategies are widely known by persons skilled in the art and are described in Lloyd-Williams P. et al., "*Convergent Solid-Phase Peptide Synthesis,*" (1993), *Tetrahedron,* 49(48), 11065-11133.

The process can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound, wherein $R_1$ has the aforementioned meaning and X is a leaving group, for example and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the peptide of formula (I) in which $R_2$ is —OH in the presence of an adequate solvent and a base such as, N,N-diisopropylethylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the peptide cleavage process from the polymeric carrier.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (CIZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), trityl (Trt), methoxytrityl (Mtt), 2,4-dinitrophenyl (Dnp), N-[1-(4,4-dimethyl-2,6-dioxocyclohex-1-ylidene)ethyl (Dde), 1-(4,4-dimethyl-2,6-dioxo-cyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt tester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-(N-[1-(4,4-dimethyl-2,6-dioxocyclohexylidene)-3-methylbutyl]amino) benzyl ester (Dmab), among others; preferred protective groups of the invention are the All, tBu, cHex, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tBu, All, Bzl or 2,6-dichlorobenzyl (2,6-diCIZ) among others. The serine side chain is protected by a protective group selected from the group consisting of tBu, Bzl, Trt and Ac. The histidine side chain can be protected by a protective group selected from the group consisting of Tos, Dnp, methyl (Me), Boc, benzyloxymethyl (Bom), Bzl, Fmoc, Mts, Trt and Mtt. The amide group of the glutamine and asparagine side chain can be protected by the Trt group or the xanthyl group (Xan) or can be used unprotected. For the protection of the carboxyl group of the aspartic acid side chain esters can be used such as tBu ester, All ester, triphenylmethyl ester (Trt ester), cHx ester, Bzl ester, ortho-nitrobenzyl ester, para-nitrobenzyl ester, para-methoxybenzyl ester, trimethylsilylethyl ester, 2-phenylisopropyl ester, Fm ester or Dmab ester, among others. For the protection of the amino group of the lysine side chain amides can be used, such as amide acetate, amide benzoate, amide pivalate; carbamates, such as Cbz or Z, CIZ, pNZ, Boc, Troc, Teoc, Fmoc or Alloc, Trt, Mtt, Dnp, Dde, ivDde, Adpoc, among others.

In a preferred embodiment, the protective group strategy used is the strategy wherein the amino groups are protected by Boc, the carboxyl groups are protected by Bzl, cHx or All esters, the tyrosine side chain is protected with 2-BrZ or Bzl, the serine side chain is protected by the Bzl group, the histidine side chain is protected by the Tos or Bom group, the glutamic acid side chain is protected by Bzl, cHx or All, glutamine and asparagine are used unprotected in their side chain and the lysine side chain is protected by CIZ, Fmoc or Alloc.

In another preferred embodiment, the protective group strategy used is the strategy wherein the amino groups are protected by Fmoc, the carboxyl groups are protected by tBu, All or Trt esters, the tyrosine side chain is protected by tBu, the serine side chain is protected by the tBu group, the histidine side chain is protected by the Trt or Mtt group, the glutamic acid side chain is protected by tBu or All, glutamine and asparagine are used protected by the Trt group in its side chain, and the lysine side chain is protected by Boc, Trt or Alloc.

Examples of these and other protective groups, their introduction and removal, can be found in the literature [Atherton, B., and Sheppard, R. C., "*Solid Phase Peptide Synthesis: A practical approach*," (1989), IRL Oxford University Press]. The term "protective groups" also includes the polymeric supports used in solid phase synthesis.

When synthesis takes place totally or partially in solid phase, the possible solid supports used in the process of the invention involve polystyrene support, polyethylene glycol grafted to polystyrene and similar, for example and not restricted to, p-methylbenzhydrylamine resins (MBNA) [Matsueda, G. R., et al., "*A p-methylbenzhydrylamine resin for improved solid-phase synthesis of peptide amides*," (1981), *Peptides*, 2, 45-50], 2-chlorotrityl resins [Barlos, K., et al., "*Darstellung geschUtzter Peptid-Fragmente unter Einsatz substituierter Triphenylmethyl-Harze*," (1989), *Tetrahedron Lett.*, 30, 3943-3946; Barlos, K., et al., "*Veresterung von partiell geschützten Peptid-Fragmenten mit Harzen. Einsatz von 2-Chlorotritylchlorid zur Synthese von Leu1-Gastrin I*," (1989), *Tetrahedron Lett.*, 30, 3947-3951], TentaGel™ resins (Rapp Polymere GmbH), ChemMatrix™ resins (Matrix Innovation, Inc) and similar, which may or may not include a labile linker, such as 5-(4-aminomethyl-3,5-dimethoxyphenoxy) valeric acid (PAL) [Albericio, F., et al., "*Preparation and application of the 5-(4-(9-fluorenylmethyloxycarbonyl) aminomethyl-3,5-dimethoxy-phenoxy) valeric acid (PAL) handle for the solid-phase synthesis of C-terminal peptide amides under mild conditions*," (1990), *J. Org. Chem.*, 55, 3730-3743], 2-[4-aminomethyl-(2,4-dimethoxyphenyl)] phenoxyacetic acid (AM) [Rink H., "*Solid-phase synthesis of protected peptide fragments using a trialkoxy-diphenyl-methylester resin*," (1987), *Tetrahedron Lett.*, 28, 3787-3790], Wang [Wang, S. S., "*p-Alkoxybenzyl Alcohol Resin and p-Alkoxybenzyloxycarbonylhydrazide Resin for Solid Phase Synthesis of Protected Peptide Fragments*," (1973), *J. Am. Chem. Soc.*, 95, 1328-1333] and similar, which enable simultaneous deprotection and cleavage of the compound from the polymeric support.

Cosmetic or Pharmaceutical Compositions of the Invention

The compounds of the invention can be administered for their application by any means that causes contact between the compounds and the site of action in a mammal's body, preferably that of a human being, and in the form of a composition which contains them.

Accordingly, a second aspect of the invention relates to a cosmetic or pharmaceutical composition which comprises at least one compound of the invention, its stereoisomers, and/or its cosmetically or pharmaceutically acceptable salts together with at least one cosmetically or pharmaceutically acceptable adjuvant or excipient. These compositions can be prepared by conventional means known to persons skilled in the art ["*Harry's Cosmeticology,*" *Seventh edition*, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically or pharmaceutically effective amount of the compounds of the invention which should be administered, as well as their dosage, will depend on numerous factors, including age, state of the patient, the nature or severity of the condition, disorder or disease to be treated and/or cared for, the route and frequency of administration and of the particular nature of the compounds to be used.

"Cosmetically and pharmaceutically effective amount" is understood to mean a non-toxic but sufficient amount of the compound or compounds of the invention to provide the desired effect. The compounds of the invention are used in the cosmetic or pharmaceutical compositions of this invention at cosmetically or pharmaceutically effective concentrations to achieve the desired effect; for example, in amounts with respect to the total weight of the composition of: from 0.00000001% (in weight) to 20% (in weight); from 0.000001% (in weight) to 15% (in weight), from 0.00001% (in weight) to 10% (in weight); or from 0.0001% (in weight) to 5% (in weight).

The compounds of general formula (I), their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the compound of the invention is administered. These cosmetic or pharmaceutical carriers can be liquids, such as water, oils or surfactants, including those of petroleum, animal, plant or synthetic origin, for example and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposheres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the compounds of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions which contain the compounds of general formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body.

Examples of fabrics, non-woven fabrics, garments, medical devices and means for immobilizing the compounds to them, among which are the delivery systems and/or the sustained release systems described above, can be found in literature and are known in the prior art [Schaab, C. K., (1986) *HAPPI* May 1986; Nelson, G., "*Application of microencapsulation in textiles*," (2002), *Int. J. Pharm.*, 242 (1-2), 55-62; "*Biofunctional Textiles and the Skin*" (2006) *Curr. Probl. Dermatol.* v.33, Hipler U. C. and Elsner P., eds. S. Karger AG, Basel, Switzerland; Malcolm R. K. et al., "*Controlled release of a model antibacterial drug from a novel self-lubricating silicone biomaterial*," (2004), *J. Cont. Release*, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic or pharmaceutical compositions which contain the compounds of the invention, their stereoisomers, mixtures thereof and/or their cosmetically or pharmaceutically acceptable salts, can be used in different types of compositions for topical or transdermal application which optionally include cosmetically or pharmaceutically acceptable excipients necessary for formulating the desired administration form.

The compositions for topical or transdermal application can be produced in any solid, liquid or semisolid formulation, such as and not restricted to, creams, multiple emulsions such as and not restricted to, oil and/or silicone in water emulsions, water-in-oil and/or silicone emulsions, water/oil/water or water/silicone/water type emulsions and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories for example and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders among others.

The cosmetic or pharmaceutical compositions of the invention may include agents which increase the percutaneous absorption of the compounds of the invention, for example and not restricted to, dimethylsulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the peptide of the invention. The application area will be determined by the nature of the condition, disorder and/or disease to be treated and/or cared for.

Furthermore, the cosmetic compositions containing the compounds of general formula (I), their stereoisomers, mixtures thereof and/or their cosmetically or pharmaceutically acceptable salts can be used in different types of formulations for oral administration, preferably in the form of oral cosmetics or drugs, such as and not restricted to, capsules, including gelatin capsules, soft capsules, hard capsules, tablets, including sugar coated tablets, tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, for example and not restricted to, fat components, aqueous components, humectants, preservatives, texturizing agents, flavors, aromas, antioxidants and colorants common in the food industry.

Cosmetic or pharmaceutical compositions containing the compounds of general formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal route, intravascular injections, such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable adjuvants contained in the cosmetic or pharmaceutical compositions described in this invention are additional ingredients commonly used in cosmetic or pharmaceutical compositions, for example and not restricted to, other DNA protecting agents, other DNA repair agents, stem cell protecting agents, agents inhibiting neuronal exocytosis, anticholinergic agents, agents inhibiting muscular contraction, antiaging agents, anti-wrinkle agents, antiperspirant agents, anti-inflammatory and/or analgesic agents, anti-itching agents, calming agents, anesthetic agents, inhibitors of acetylcholine-receptor aggregation, inhibitors of acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, detoxifying agents, antihistamine agents, antiviral agents, antiparasitic agents, emulsifiers, emollients, organic solvents, liquid propellants, skin conditioners, humectants, substances which retain moisture, alpha hydroxy acids, beta hydroxy acids, moisturizers, hydrolytic epidermal enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, desquamating agents, antimicrobial agents, antifungal agents, fungistatic agents, bactericidal agents, bacteriostatic agents, agents stimulating the synthesis of dermal or epidermal macromolecules and/or capable of inhibiting or preventing their degradation, collagen synthesis-stimulation agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, AQP-3 modulating agents, aquaporin synthesis-stimulating agents, proteins of the aquaporin family, hyaluronic acid synthesis-stimulating agents, glycosaminoglycan synthesis-stimulating agents, fibronectin synthesis-stimulating agents, sirtuin synthesis-stimulating agents, sirtuin-activating agents, heat shock proteins, heat shock protein synthesis-stimulating agents, agents stimulating the synthesis of lipids and components of the stratum corneum, ceramides, fatty acids, agents that inhibit collagen degradation, agents that inhibit matrix metalloproteinase, agents that inhibit elastin degradation, agents that inhibit serine proteases such as kallikreins, elastase or cathepsin, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriatic agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α expression, agents modulating the activity of PPARγ, agents which increase or reduce the triglyceride content of adipocytes, anti-cellulite agents, agents which inhibit PAR-2 activity, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, agents delaying hair loss, preservatives, perfumes, cosmetic and/or absorbent and/or body odor-masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided they are physically and chemically compatible with the rest of components of the composition and in particular with the compounds of the invention. Furthermore, the nature of these additional ingredients should not unacceptably alter the benefits of the compounds of this invention. The nature of these additional ingredients can be synthetic or natural, such as plant extracts, or come from a biotechnological process or from a combination of a synthetic procedure and biotechnological process. Additional examples can be found in *CTFA International Cosmetic Ingredient Dictionary & Handbook*, 12th Edition (2008). In the context of this invention, biotechnological process is understood to be any process that produces the active ingredient, or part of it, in an organism, or in part of it.

In a particular embodiment, the anti-wrinkle agent and/or anti-aging agent is selected, for example and not restricted to, from the extracts or hydrolyzed extracts of *Vitis vinifera, Rosa canina, Curcuma longa, Theobroma cacao, Glnkgo biloba, Leontopodium alpinum* or *Dunaliella salina* among others, Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6 [INCI: Glycerin, Water, Hydroxypropyl Cyclodextrin, Palmitoyl Tripeptide-38], Essenskin™ [INCI: calcium hydroxymethionine], Renovage™ [INCI: Teprenone], Resistem™ [INCI: Globularia Cordifolia Ferment], Dermaxyl® [INCI: Palmitoyl Oligopeptide], Calmosensine™ [INCI: Butylene Glycol, Acetyl Dipeptide-1 Cetyl Ester], Volulip™ [INCI: Cetearyl Ethylhexanoate, Sorbitan Isostearate, Portulaca Pilosa Extract, Sucrose Cocoate, Palmitoyl Tripeptide-38], Subliskin™ [INCI: Sinorhizobium Meliloti Ferment, Cetyl Hydroxyethyl Cellulose, Lecithin], Biopeptide CL [INCI: Palmitoyl Oligopeptide], Biopeptide EL [INCI: Palmitoyl Oligopeptide], Rigin™ [INCI: Palmitoyl Tetrapeptide-3], Biobustyl™ [INCI: Glyceryl Polymethacrylate, Rahnella/Soy Protein Ferment, Palmitoyl Oligopeptide], Dynalift™ [INCI: Sodium Polystyrene Sulfonate, Sorghum Bicolor Stalk Juice, Glycerin], Idealift™ [INCI: Acetyl Dipeptide-1 Cetyl Ester], Siegesbeckia [INCI: Siegesbeckia Orientales Extract], Ovaliss™ [INCI: Coco-glucoside, Caprylyl Glycol, Alcohol, Glaucine], Juvinity™ [INCI: Geranylgeranyisopropanol] or Resistem™ [INCI proposed: Globularia Cordifolia Ferment] marketed by Sederma/Croda, Vialox® [INCI: Pentapeptide-3], Syn®-Ake® [INCI: Dipeptide Diaminobutyroyl Benzylamide Diacetate], Syn®-Coll [INCI: Palmitoyl Tripeptide-5], Phytaluronate™ [INCI: Locust Bean (*Ceratonia siliqua*) Gum], Preregen® [INCI: *Glycine soja* (Soybean) Protein, Oxido Reductases], Pepha-Nutrix™ [INCI: Natural Nutrition Factors], Pepha-Tight™ [INCI: Algae Extract, Pullulan], Pentacare-NA™ [INCI: Hydrolyzed Wheat Gluten, Ceratonia Siliqua Gum], Syn®-Tacks [INCI: Glycerin, Palmitoyl Dipeptide-5 Diaminobutyloyl Hydroxythreonine, Palmitoyl Dipeptide-6 Diaminohydroxybutyrate], BeauActive™ MTP [INCI: Hydrolyzed milk protein], Syn®-TC [INCI: Tetradecyl Aminobutyroylvalylaminobutyric Urea Trifluoroacetate, Palmitoyl Tripeptide-5, Palmitoyl Dipeptide-5 Diaminobutyroyl Hydroxythreonine], Syn®-Hycan [INCI: Tetradecyl Aminobutyroylvalylaminobutyric Urea Trifluoroacetate], Syn®-Glycan [INCI: Tetradecyl Aminobutyroylvalyl-aminobutyric Urea Trifluoroacetate], Regu-Age™ [INCI: Hydrolyzed Rice Bran Protein, Oxido Reductases, Glycine Soja Protein], Pepha-Timp™ [INCI: Human oligopeptide-20], Colhibin™ [INCI: Hydrolyzed Rice Protein], Elhibin™ [INCI: Glycine Soja Protein, Disodium cocoamphodiacetate] or All-Q™ Plus [INCI: Ubiquinone, Tocopheryl Acetate] marketed by Pentapharm/DSM, Myoxinol™ [INCI: Hydrolyzed *Hibiscus esculentus* Extract], Syniorage™ [INCI: Acetyl Tetrapeptide-11], Dermican™ [INCI: Acetyl Tetrapeptide-9], DN-AGE® LS [INCI: *Cassia alata* leaf Extract], Hyalufix™ GL [INCI: Alpinia Galanga Leaf Extract], Neurobiox™ [INCI: Achillea Millefolium Extract,], Deliner™ [INCI: *Zea mays* (Corn) Kernel Extract], Lys'Iastine™ V [INCI: Peucedanum Graveolens (Dill) Extract], Extracellium [INCI: Hydrolyzed Potato Protein], Proteasyl™ TP LS 8657 [INCI: Pisum Sativum Extract], Flavagrum™ PEG [INCI: PEG-6 Isostearate, Hesperetin Laurate], Micromerol™ [INCI: Pyrus Malus Fruit Extract], Extracellium™ [INCI: Hydrolyzed Potato Protein], Marine Filling Spheres [INCI: Pentaerythrityl Tetraisostearate, Silica Dimethyl Silylate, Sodium Chondroitin Sulfate, Atelocollagen], Triactigen™ [INCI: Mannitol, Cyclodextrin, Yeast Extract, Disodium Succinate], Eterniskin™ [INCI: Grifola Frondosa Fruiting Body Extract, Maltodextrin], Ascotide™ [INCI: Ascorbyl Phosphate Succinoyl Pentapeptide-12], Hyalurosmooth™ [INCI: Cassia Angustifolia Seed Polysaccharide], Indinyl™ [INCI: Cassia Angustifolia Seed Polysaccharide], Arganyl™ [INCI: Argania Spinosa Leaf Extract], Sphingoceryl™ Veg [INCI: Phyto-ceramides], Vit-A-Like™ [INCI: Vigna Acontifolia Seed Extract], Peptiskin [INCI: Arginine/Lysine polypeptide], Prodejine™ [INCI: Mannitol, Cyclodextrin, Yeast Extract, Disodium Succinate], Aqu'Activ™ [INCI: Behenyl Alcohol, Glyceryl Oleate, Cocamide MIPA, Calcium Citrate], Elestan™ [INCI: Glycerin, Manilkara Leaf Extract], Hibiscin™ HP [INCI: Hibiscus Esculentus Seed Extract] or Litchiderm™ [INCI: Litchi Chinensis Pericarp Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline® [INCI: Acetyl Hexapeptide-30], Aldenine® [INCI: Hydrolized Wheat Protein, Hydrolized Soy Protein, Tripeptide-1], Preventhelia® [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase® [INCI: Acetylarginyltriptophyl Diphenylglycine], Thermostressine® [INCI: Acetyl Tetrapeptide-22], Lipochroman™ [INCI: Dimethylmethoxy Chromanol], Chromabright® [INCI: Dimethylmethoxy Chromanyl Palmitate], Antarcticine® [INCI: Pseudoalteromonas Ferment Extract], dGlyagee [INCI: Lysine HCl, Lecithin, Tripeptide-9 Citrulline], Vilastene™ [INCI: Lysine HCl, Lecithin, Tripeptide-10 Citrulline], Hyadisine® [INCI: Pseudoalteromonas Ferment Extract], Hyanify™ [INCI: Saccharide Isomerate], Diffuporine® [INCI: Acetyl Hexapeptide-37], Silusyne® [INCI: Soybean (Glycine Soja) Oil, Sorbitan Sesquioleate, Isohexadecane, Sodium Hyaluronate, Lauryldimonium Hydroxypropyl Hydrolized Soy Protein, Acetyl Hexapeptide-39], Adifyline® [INCI: Acetyl Hexapeptide-38], Delisens™ [INCI: Acetyl Hexapeptide-46] or Telangyn™ [INCI: Acetyl Tetrapeptide-40] marketed by Lipotec/Lubrizol, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract], Quintescine™ IS [INCI: Dipeptide-4], Peptide Vinci 01 [INCI: Penta-decapeptide-1], Peptide Vinci 02™ [INCI: Hexapeptide-3], Aquarize IS™ [INCI: Hydrolyzed Rice Extract], Lanablue™ [INCI: Algae extract], Ederline™ [INCI: Pyrus Malus (Apple) Seed Extract], Dynachondrine™ ISR [INCI:Hydrolized Soy Protein], Prolixir S20™ [INCI: Dimer Tripeptide-43], Phytocohesine™ PSP [INCI: Sodium Beta-Sitosteryl Sulfate, Beta-Sitosterol], Perenityl™ IS [INCI: Pyrus Communis (Pear) Seed Extract], Caspaline 14™ [INCI: Hexapeptide-42], Peptide Q10™ [INCI:Pentapeptide-34 Trifluoroacetate], Survixyl^IS™ [INCI: Pentapeptide-31], ChroNOgen™ [INCI: Tetrapeptide-26] or Telosense™ [proposed INCI: Hydrolized Soy Protein, Hydrolized Yeast Protein] marketed by Vincience/ISP/Ashland, BONT-L-Peptide™ [INCI: Palmitoyl Hexapeptide-19], TIMP Peptide [INCI: Acetylhexapeptide-20], ECM Moduline™ [INCI: Palmitoyl Tripeptide-28], Renaissance™ [INCI: Hydrolyzed Wheat Protein, Palmitoyl Decapeptide-21, Decapeptide-22, Oligopeptide-78, Zinc Palmitoyl Nonapeptide-14] marketed by Infinitec Activos, Deepaline™ PVB [INCI: Palmitoyl hydrolyzed Wheat Protein], Sepilift® DPHP [INCI: Dipalmitoyl Hydroxyproline], Survicode [INCI: Sodium Cocoyl Alaninate], Aquaxyl™ [INCI: Xylitylglucoside, Anhydroxylitol, Xylitol] or Lipacide™ PVB [INCI: Palmitoyl hydrolyzed Wheat Protein] marketed by Seppic, Gatuline® Expression [INCI: *Acmella oleracea* Extract], Gatuline® In-Tense [INCI: *Spilanthes acmella* Flower Extract] or Gatuline® Age Defense 2 [INCI: *Juglans regia* (Walnut) Seed Extract] or Hematite™ [INCI: Hematite] marketed by Gattefossé, Thalassine™ [INCI: Algae Extract] marketed by Biotechmarine, ChroNOline™ [INCI: Caprooyl Tetrapeptide-3], Lanablue® [INCI: Algae Extract], Exo-H [INCI: Alteromonas Exopolysaccharide Extract], Exo-T™ [INCI: Vibrio Exopolysaccharide Extract], Hydriame® [INCI: Water, Glycosaminoglycans, Sclerotium Gum], MDI Complex® [INCI: Glycosaminoglycans], Adipofill™ [INCI: Ornithine, Phospholipids, Glycolipids] or Thymulen® 4 [INCI: Acetyl Tetrapeptide-2] marketed by Atrium/Unipex Innovations/Lucas Meyer Cosmetics, EquiStat™ [INCI: *Pyrus malus* Fruit Extract, *Glycine soja* Seed Extract], Juvenesce™ [INCI: Ethoxydiglicol and Caprylic Triglyceride, Retinol, Ursolic Acid, Phytonadione, Ilomastat], Ursolisome™ [INCI: Lecithin, Ursolic Acid, Atelocollagen, Xanthan Gum, Sodium chondroitin sulfate], Basaline™ [INCI: Hydrolyzed Malt Extract], Phytokine™ [INCI: Hydrolyzed Soy Protein], marketed by Coletica/Engelhard/BASF, Ameliox™ [INCI: Carnosine, Tocopherol, *Silybum marianum* Fruit Extract] or PhytoCellTec™ Malus Domestica [INCI: *Malus domestica* Fruit Cell Culture], Lipobelle Soyaglicane™ [INCI: Soy Isoflavones] or DermCom™ [INCI: Crocus Chrysanthus Bulb Extract, Acacia Senegal Gum, Aqua/Water] marketed by Mibelle Biochemistry, Bioxilift™ [INCI: Pimpinella anisum Extract], Papilactyl™ D [Cyperus Esculentus Tuber Extract], SMS Anti-Wrinkle® [INCI: Annona squamosa Seed Extract], Astressyl™ [INCI: Salix Alba (Willow) Leaf Extract], Pro-Coll-One+™ [INCI: Hydrolyzed Soy Protein], Ridulisse C [INCI: Soybean], Raffermine™ [INCI: Hydrolyzed Soy Flour], Toniskin™ [INCI: Yeast Extract] or Coheliss™ [INCI: Arabinoxylans purified from Rye Seeds], marketed by Silab, ActiMatrix [INCI: Peptide based mushroom Extract], Peptamide 6 [INCI: Hexapeptide-11] marketed by Active Organics/Arch, HPS3 [Paraffinum Liquidum, Padina Pavonica Thalllus Extract] marketed by Alban Muller, DermaPep™ A420 [INCI: Myristoyl Tetrapeptide-6, Glycerin, Butylene Glycol] and DermaPep A350 [INCI: Myristol Tripeptide-31, Butylene Glycol] marketed by Dermapep, Phytosphingosine™ SLC [INCI: Salicyloyl Phytosphingosine], TEGO Pep 4-17™ [INCI: Tetrapeptide-17], Granactive™ AGE [INCI: Palmitoyl Hexapeptide-14, Lycium Barbarum Fruit Extract (Goji Berry)], Sphingokine™ NP [INCI: Caprooyl Phytosphigonsine], TEGO Pep 4-Even™ [INCI: Glycerin, Tetrapeptide-30] marketed by Evonik Goldschmidt, Collageneer™ [INCI: Helianthus Annuus Seed Oil, Lupinus Albus Extract], Effipulp™ [INCI: Hydrolyzed Avocado Protein] or Actimp™ 1.9.3 [INCI: Hydrolyzed Lupine Protein] marketed by Expanscience Laboratorie, ECM Protect [INCI: Tripeptide-2] or Glycosann™ [INCI: Sodium Chondroitin Sulfate] marketed by IEB, Ronacare Cyclopeptide-5 [INCI: Ectoin, Cyclopeptide-5] marketed by Merk, Ascotide™ [INCI: Ascorbyl Phosphate Succinoyl Pentapeptide-12] marketed by Peptron, Homeostatine™ [INCI: Enteromorpha Compressa, Caesalpinia Spinosa], Pronalen™ Firming [INCI: Lady's Thistle Extract, Lady's Mantle Extract, Horsetail Extracti, Soy Germ Extract, Wheat Germ Extract, Alfalfa Extract, Radish Extract, Water (Aqua), Butylene Glycol, Decyl Glucoside] and Vitasource™ [INCI: Propanediol, Water, Baicalin] marketed by Provital, Reforcyl™ [INCI: Glutamine, Decyl Glucoside, Phenethyl Alcohol, Cistus Incanus Flower/Leaf/Stem Extract, Gynostemma Pntaphyllum Leaf/Stem Extract], Proteolea™ [INCI: Levan, Decyl Glucoside, Olea Europaea Leaf Extract, Phenethyl Alcohol, Zizyphus Jujuba Seed Extract] and Vitaderm™

[INCI: Hydrolyzed Rice Protein, Ilex Aquafolium Extract, Sodium Ursolate, Sodium Oleanolate] marketed by Rahn, Peptiskin™ [INCI: Arginine/Lysine polypeptide], Nuteline™ C [INCI: Hydrolyzed Hazelnut Protein] and Radicaptol™ [INCI: Propylene Glycol, Water, Passiflora Incarnate Extract, Ribes Nigrum Leaf Extract, Vitis Vinifera Leaf Extract] marketed by Solabia, StimulHyal™ [INCI: Calcium Ketogluconate], Dakaline™ [INCI: Prunus Amygdalus Dulcis, Anogeissus Leiocarpus Bark Extract], RenovHyal™ [INCI: Sodium Hyaluronate] and Viapure Boswellia [INCI: Boswellia *Serrata* Extract] marketed by Soliance, SymPeptide™ 222 [INCI: Myristoyl Pentapeptide-8], SymPeptide™ 225 [INCI: Myristoyl Pentapeptide-11], SymPeptide™ 239 [INCI: Myristoyl Octapeptide-1], SymPeptide™ 230 [INCI: Myristoyl Hexapeptide-4] marketed by Symrise, antagonists of the $Ca^{2+}$ channel for example and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives and/or salts, carnosine and its derivatives, DNA repair enzymes for example and not restricted to, photolyase or T4 endonuclease V, or chloride channel agonists among others, and/or mixtures thereof.

In another particular embodiment, the agent capable of filtering UV and IRA rays is selected, for example and not restricted to, from the group consisting of photoprotectors of an organic or mineral nature active against ultraviolet A and/or B rays such as substituted benzotriazoles, substituted diphenyl acrylates, organic complexes of nickel, umbelliferone, urocanic acid, derivatives of biphenyl, e-stilbene, 3-benzylidene camphor, and their derivatives such as 3-(4-methylbenzylidene)camphor; derivatives of 4-aminobenzoic acid, 2-ethylhexyl 4-(dimethylamino)benzoate, 2-octyl 4-(dimethylamino)benzoate and amyl 4-(dimethylamino) benzoate; cinnamic acid esters, such as 2-ethylhexyl 4-methoxycinamate or diethylamino hydroxybenzoyl hexyl benzoate, propyl 4-methoxycinnamate, isoamyl 4-methoxycinnamate, 2-ethylhexyl 2-cyano-3,3-phenyl cinnamate (octocrylenes); salicylic acid esters, such as 2-ehtylhexyl salicylate, 4-isopropyl benzyl salicylate, homomenthyl salicylate; derivatives of benzophenone, such as 2-hydroxy-4-methoxybenzophenone, 2-hydroxy-4-methoxy-4'-methylbenzophenone, 2,2'-dihydroxy-4-methoxybenzophenone; benzalmalonic acid esters, such as di-2-ethylhexyl 4-methoxybenzalmalonate; derivatives of triazine, such as 2,4,6-trianilino, p-carbo-2'-ethyl-1'-hexyloxy-1,3,5-triazine, octyl triazone or dioctylbutamidotriazones; propane-1,3-diones, such as 1-(4-tert-butylphenyl)-3-(4'-methoxyphenyl)propane-1,3-dione, derivatives of ketotricyclo(5.2.1.0) decane, 2-phenylbenzimidazole-5-sulfonic acid; derivatives of benzophenone sulfonic acid, such as 2-hydroxy-4-methoxybenzofenone-5-sulfonic acid and its salts; 4-(2-oxo-3-bornylidenemethyl)benzenesulfonic acid, derivatives of benzoylmethane, such as benzoylmethane 2-methyl-5-(2-oxo-3-bornylidene)sulfonic acid, such as 1-(4'-tert-butylphenyl)-3-(4'-methoxyphenyl)propane-1,3-dione, 4-tert-butyl-4'-methoxydibenzoylmethane, 1-phenyl-3-(4'-isopropylphenyl)-propane-1,3-dione, compounds of enamine, anthranilates, silicones, derivatives of benzimidazole, imidazolines, derivatives of benzo allyl, Chromabright® [INCI: Dimethylmethoxy Chromanyl Palmitate] or Preventhelia® [INCI: Diaminopropionoyl Tripeptide-33] both marketed by Lipotec, metal oxides such as zinc, titanium, iron, zirconium, silicon, manganese, aluminium and cerium oxides; silicates, talc, barium sulfate, zinc stearate, carbon nanotubes and/or mixtures thereof.

In another particular embodiment, the whitening or depigmenting agent or melanin synthesis inhibiting agent, is selected, for example and not restricted to from the extracts of *Achillea millefolium*, *Aloe vera*, *Aradirachta indica*, *Asmuna japonica*, *Autocarpus incisus*, *Bidens pilosa*, *Broussonetia papyrifera*, *Chlorella vulgaris*, *Cimicifuga racemosa*, *Emblica officinalis*, *Glycyrrhiza glabra*, *Glycyrrhiza uralensis*, *Ilex purpurea*, *Ligusticum lucidum*, *Ligusticum wallichii*, *Mitracarpus scaber*, *Morinda citrifolia*, *Morus alba*, *Morus bombycis*, *Naringi crenulata*, *Prunus domesticus*, *Pseudostellariae radix*, *Rumex crispus*, *Rumex occidentalis*, *Sapindus mukurossi*, *Saxifragia sarmentosa*, *Scutellaria galericulate*, *Sedum sarmentosum bunge*, *Stellaria medica*, *Triticum vulgare*, *Arctostaphylos Uva ursi* or *Whitania somnifera* among others and/or Lipochroman™ [INCI: Dimethylmethoxy Chromanol], Chromabright® [INCI: Dimethylmethoxy Chromanyl Palmitate] marketed by Lipotec/Lubrizol, Whitami [INCI: Maltodextrin, Papain, Titanium Dioxide, Angelica Acutiloba Root Extract, Saposhnikovia Divaricata Root Extract, Thioctic Acid, Kaolin, Ascorbyl Glucoside, Pinus Pinaster Bark Oligomeric Proanthocyanidins] marketed by Alban Muller; NAB® Asafetida Extract [INCI: Aqua (Water), Butylene Glycol, Ethoxydiglycol, Ferula Foetida Extract] marketed by Arch; Licorice Roots Extract [INCI: Licorice (Glycyrrhiza Glabra) Extract] marketed by Campo Research; Belides™ [INCI: Bellis Perennis (Daisy) Flower Extract] marketed by CLR; Algowhite [INCI: Ascophyllum Nodosum Extract] marketed by Codif; Biowhite™ [INCI: Saxifraga Sarmentosa Extract, Vitis Vinifera (Grape) Fruit Extract, Butylene Glycol, Water, *Morus bombycis* Root Extract, Scutellaria Baicalensis Root Extract, Disodium EDTA], Melarrest® A [INCI: Glycerin, Lactic Acid, Kojic Acid, Ascorbic Acid], Melarrest® L [INCI: Water, Cyclopentasiloxane, Butylene Glycol, Propylene Glycol, Phospholipids, Glycyrrhiza Glabra (Liquorice) Extract, Kojic Acid, Ammonium Glycyrrhizate], Vitagen™ [INCI: Aminopropyl Ascorbyl Phosphate] or Collalift™ [INCI: Hydrolyzed Malt Extract], marketed by Coletica/Engelhard/BASF; DC Skin Bright™ [INCI: PEG-12 Glyceryl Distearate, Methyl Dihydroxybenzoate, Ethoxydiglycol, Polyethylene, Water] marketed by DC Ingredients; DS-WHITEKLE™ [INCI: Acetylphytosphingosine] marketed by Doosan; TEGO Cosmo C™ 250 [INCI: 1-methylhydantoine-2-imide] and TEGO Pep 4-Even™ [INCI: Glycerin, Tetrapeptide-30] marketed by Evonik Goldschmidt; Albatin® [INCI: Aminoethylphosphinic Acid, Butylene Glycol, Water] marketed by Exsymol; Synerlight™ [INCI: Actinidia Chinensis (Kiwi) Fruit Water, Butylene Glycol, Alcohol, Sophora Angustifolia Root Extract] marketed by Gattefossé; Clerilys™ [INCI: Water, Cucumis Santivus, Morus Alba Extract, Hibiscus Sabdariffa Extract, Wine Extract] marketed by Greentech; Melanostatine®-5 [INCI: Dextran, Nonapeptide-1] marketed by IEB/Unipex; Actiwhite™ [INCI: Water, Glycerin, Sucrose Dilaurate, Polysorbate 20, Pisum Sativum Extract], Active® Powder Whiteness [INCI: Water, Lauryl Methacrylate/Glycol Dimethacrylate Copolymer, Butylene Glycol, Dicaprylyl Ether, Titanium Dioxide, Algae, Citric Acid, Sodium Citrate, Waltheria Indica Leaf Extract, Ferulic Acid, Polyglyceryl-2-Di polyhydroxystearate], Dermawhite® NF LS 9410 [INCI:Mannitol, Sodium Gluconate, Citric Acid, Sodium Citrate, Waltheria Indica Leaf Extract, Dextrin, Ferulic Acid], Radianskin™ [INCI: Hydroxyphenoxy Propionic Acid] marketed by L. Serobiologiques/Cognis/BASF; Lipobrite® HCA-4 [INCI:PEG-4, Hydroxycinnamic Acid] marketed by Lipochemicals; Whitessence™ [INCI: Artocarpus Heterophyllus Seed Extract, Maltodextrin, Disodium Phosphate, Sodium Phosphate] marketed by Lucas Meyer; Emblica™ [INCI: Phyllanthus Emblica Fruit Extract] marketed by Merck; SulforaWhite™ [INCI: Lepidium Sativum Sprout Extract, Glycerin, Lecithin, Phenoxyethanol, Aqua], Delentigo™ [INCI: Lepidium Sativum Sprout Extract, Lecithin, Soy Isoflavones, Polysorbate 80, Alcohol, Glycerin, Phenoxyethanol, Water] marketed by Mibelle; Alpha-Arbutin [INCI: Alpha-arbutin], Gigawhite™ [INCI:Water, Glycerin, Malva Sylvestris (Mallow) Extract, Mentha Piperita Leaf Extract, Primula Veris Extract, Alchemilla Vulgaris Extract, Veronica Officinalis Extract, Melissa Officinalis Leaf Extract, Achillea Millefolium Extract], Melawhite® [INCI: Leukocyte Extract, AHA], Melfade®-J [INCI:Water, Arctostaphylos Uva-Ursi Leaf Extract, Glycerin, Magnesium Ascorbyl Phosphate] or Regu-Fade™ [INCI: Resveratrol] marketed by Pentapharm/DSM; CellActive® White [INCI: Aqua, Alcohol denat., Niacinamide, Zinc PCA, Chlorella Vulgaris/Lupinus Albus Protein Ferment, Nasturtium Officinale Extract] Illumiscin® [INCI:Glycerin, Aqua (Water), Olea Europaea Leaf Extract, Ascorbyl Glucoside, Zinc PCA] marketed by Rahn; Arlatone™ Dioic DCA [INCI: Octadecenedioic Acid, BHT], Etioline™ [INCI:Glycerin, Butylene Glycol, Arctostaphylos Uva Ursi Leaf Extract, Mitracarpus Scaber Extract], Lumiskin™ [INCI:Caprylic/Capric Triglyceride, Diacetyl-Boldine], Melaclear™ 2 [INCI:Glycerin, Water, Dithiaoctanediol, Gluconic Acid, Sutilains, Beta-carotene], Lumisphere™ [INCI:Water (Aqua), Titanium Dioxide, Polysorbate 20, Cetyl Hydroxyethylcellulose, Polymethylmethacrylate, Trilaurin, Diacetyl boldine], O.D.A.White™ [INCI:Octadecenedioic Acid], Wonderlight™ [INCI:Humulus Lupulus (Hops) Strobile] marketed by Sederma/CRODA; Sepiwhite™ MSH [INCI:Undecylenoyl phenylalanine], Sepicalm™ VG [INCI:Sodium palmitoyl proline, Nymphaea Alba Flower Extract] marketed by Seppic; Clariskin II [INCI:Triticum Vulgare Extract], Dermalight® [INCI:Tropaeolum Majus Extract], Whitonyl® [INCI:Palmaria Palmata Extract] marketed by Silab; DermaPep™ A350 [INCI: Myristol Tripeptide-31, Butylene Glycol] or DermaPep™ W411 [INCI: Palmitoyl Hexapeptide-36, Methyl Undecenoyl Leucinate, Butylene Glycol] marketed by Dermapep, Neurolight.61G™ [INCI: Glycerin, Water, Pancratium Maritimum Extract] marketed by Codif, Azeloglicina® [INCI:Potassium Azelaoyl Diglycinate] marketed by Sinerga; Whitesphere Premium™ [INCI:Sucrose Palmitate, Butylene Glycol, Glyceryl Linoleate, Prunus Amygdalus Dulcis, Almond Oil, Water (aqua), Glycyrrhiza Glabra (Liquorice) Root Extract, Magnesium Ascorbyl Phosphate, Undaria Pinnatifida Extract], Axolight™ [INCI:Triticum Aestivum Extract] marketed by Soliance; SymWhite® [INCI:Phenylethyl Resorcinol], Extrapone™ Nutgrass GW [INCI:Cyperus Rotundus Root Extract] marketed by Symrise; Synovea® HR [INCI:Hexylresorcinol] marketed by Sytheon; β-White [INCI:Water, Butylene Glycol, Hydrogenated Lecithin, Sodium Oleate, Oligopeptide-68, Disodium EDTA] marketed by Unipex; Achromaxyl™ [INCI:Brassica Napus Extract] marketed by Vincience/ISP; arbutin and its isomers, kojic acid and its derivatives, vitamin C and its derivatives, for example and not restricted to, 6-O-palmitoyl ascorbic acid, dipalmitoyl ascorbic acid, magnesium salt from ascorbic-2-phosphate acid (MAP), sodium from ascorbic-2-phosphate acid (NAP), ascorbyl glucoside or ascorbyl tetraisopalmitate (VCIP) among others, retinol and its derivatives, including tretinoin and isotretinoin, idebenone, hydroxybenzoic acid and its derivatives, flavonoids, soy extract, extract of lemon, extract of orange, extract of ginkgo, extract of cucumber, extract of geranium, extract of bearberry, extract of carob, extract of cinnamon, extract of marjoram, extract of rosemary, extract of clove, soluble extract of liquorice, extract of blackberry leaf, niacinamide, liquiritin, resorcinol and its derivatives, hydroquinone, α-tocopherol, γ-tocopherol, azelaic acid, resveratrol, mercury salts, linoleic salts, α-lipoic acid, dihydrolipoic acid, alpha hydroxy acids, beta hydroxy acids, ellagic acid, ferulic acid, cinnamic acid, oleanolic acid, aloesin and its derivatives and/or inhibitors of serine protease activity, for example and not restricted to, inhibitors of tryptase, trypsin or PAR-2 activity, among others.

In another particular embodiment, a DNA protecting agent, DNA repair agent, and/or stem cell protecting agent is selected, for example and not restricted to, from the group consisting of GP4G™ SP [INCI: Aqua, Glycerin, Aretmia Extract], Heliostatine™ [INCI: Aqua, Glycerin, Pisum Sativum Extract], Orsirtine™ [INCI: Aqua, Glycerin, Oryza Sativa Extract], Chronogen™ [INCI: Aqua, Butylene Glycol, Tetrapeptide (INCI proposed)], Survixyl™ IS [INCI: Water, Butylene Glycol, Pentapeptide-31] and Chrondricare™ [INCI: Aqua, Butylene Glycol Pentapeptide-28] marketed by Vincience/ISP/Ashland; Lanacityn® [INCI: Glycerin, Aqua, Alteromonas ferment extract, Chysanthellum indicum extract] marketed by Atrium Innovations/Lucas Meyer Cosmetics; Repair Complex [INCI: Bifida Ferment Lysate] marketed by CLR; Phycojuvenine™ [INCI: Laminaria Digitata] marketed by Codif; Unirepair™ T-43 [INCI: Butylene Glycol, Acetyl Tyrosine, Proline, Hydrolyzed Vegetable Protein, Adenosine Triphosphate] marketed by Induchem, Dragosine™ [INCI: Carnosine] marketed by Symrise; DN-Age™ [INCI: Cassia Alata Leaf Extract] marketed by Laboratories Serobiologiques/Cognis/BASF; Helioguard™ [INCI: Porphyra Umbilicalis encapsulated into liposomes], PhytoCellTec™ Malus Domestica [INCI: PhytoCellTec Malus Domestica] or PhytoCellTec Argan [INCI: Argania Spinosa Sprout Cell Extraxt, Isomalt, Lecithin, Sodium Benzoate, Aqua] marketed by Mibelle Biochemistry; Pepha-Protect™ [INCI: Water Melon Extract] marketed by Pentapharm/DSM; Celligent™ [INCI: Helianthus Annuus Seed Oil, Ethyl Ferulate, Polyglyceryl-5 Trioleate, Rosmarinus Officinalis Leaf Extract, Aqua, Disodium Uridine Phosphate] or Defensil™ [INCI: Octyl Dodecanol, Echium Plantagineum Seed Oil, Cardiospermum Halicacabum Extract, Helianthus Annuus Seed Oil Unsaponifiables] marketed by Rahn; Venuceane™ [INCI: Thermus Thermophilus Ferment, Glycerin], UV-Soft™ [INCI: Yeast Extract], Renovage™ [INCI: Caprylic/Capric Triglyceride, Teprenone], Juvinity™ [INCI: Caprylic/Capric Triglyceride, Geranylgeranylpropanol (proposed)], Phytessence Holyherb™ [INCI: Butylene Glycol, Eriodictyon Californicum (Holyherb) Flower/Leaf/Stem Extract] or Resistem [INCI: Glycerin, Globularia Cordifolia Ferment] marketed by Sederma/Croda; and Heliomoduline™ [INCI: Low molecular weight peptides from cottonseed] or Stem-C-Guard™ [Hydrolyzed Pea] marketed by Silab.

In another particular embodiment, the reactive carbonyl species scavenger, free radical scavengers and/or anti-glycation agent, detoxifying agent, antioxidant and/or anti-pollution agent is selected, for example and not restricted to, from the group consisting of carnosine and its derivatives, GHK [INCI: Tripeptide-1] and its salts and/or derivatives, Quintescine™ IS [INCI: Dipeptide-4] marketed by Vincience/ISP/Ashland; Melitane™ [INCI: Dextran, Acetyl Hexapeptide-1], Homeoxy™ [INCI: Enteromorpha Compressa, Palmaria Palmata Extract] or Lanatellis™ [INCI: Glycerin, Aqua, Chrysantellum Indicum Extract, Camellia Sinensis Leaf Extract] marketed by Atrium Innovations/

Lucas Meyer Cosmetics; Protectan™ [INCI: Lactococcus Ferment Lysate] marketed by CLR; Phycosaccharide™ [INCI: Water, Hydrolyzed Algin, Magnesium Sulfate, Manganese Sulfate] or Algowhite™ [INCI: Water, Ascophyllum Nodosum Extract] marketed by Codif; Preregen™ [INCI: Glycine Soja (Soybean) Protein, Oxido Reductases], Edelweiss™ GC [INCI: Leontopodium Alpinum Extract], Lipogard™ [INCI: Squalane, Ubiquinone], Nectapure™ [INCI: Buddleja Davidii Extract, Thymus Vulgaris Extract], Alpaflor Nectapure™ [INCI: Buddleja Davidii Extract, Thymus Vulgaris Extract, Glycerin, Water] or Dismutin-BT™ [INCI: Highly purified SOD from a natural yeast strain of *Saccharomyces cerevisiae*] marketed by Pentapharm/DSM; TEGO Turmerone™ [INCI: Curcuma Longa Extract] marketed by Evonik Goldschmidt; Hierogaline™ [INCI: Triticum Vulgare (Wheat) germ oil unsaponifiables, Sesamum Indicum (Sesame) oil unsaponifiables] marketed by Expanscience Laboratoires; Glistin™ [INCI: Glutamylamidoethyl Indole, Aqua], Glutrapeptide™ [INCI: Aqua, Pyroglutamylamidoethyl Indole], Algisium™ C [INCI: Methylsilanol Mannuronate], Silysin™ C [INCI: Silanetriol Lysinate], Exsy-Arl™ [INCI: Prolinamidoethyl Imidazole, Butylene Glycol, Aqua] or OTZ-10™ [INCI: Aqua, Oxothiazolidine] marketed by Exsymol; Gatuline Skin-Repair Bio [INCI: Alcohol, Water, Onopordum Acanthium Flower/Leaf/Stem extract] marketed by Gattefossé; Preventhelia® [INCI: Diaminopropionoyl Tripeptide-33], Aldenine® [INCI: Hydrolized Wheat Protein, Hydrolized Soy Protein, Tripeptide-1], Lipochroman™ [INCI: Dimethylmethoxy Chromanol], Thermostressine® [INCI: Acetyl Tetrapeptide-22] or Bodyfensine® [INCI: Acetyl Dipeptide-3 Aminohexanoate] marketed by Lipotec/Lubrizol; Setiline™ [INCI: Hydrolyzed Trigonella Foenum-Graecum Seed Extract] marketed by Greentech; Sunactyl™ [INCI: Mannitol, Pisum Sativum Extract, Histidine HCl, Arginine, Cyclodextrin, Dextrin, Yeast Extract, Acetyl Tyrosine, Pyridoxine HCl, Khaya Senegalensis Bark Extract™, Nicotinamide, Adenine Dinucleotide, Disodium Succinate, Aspartic Acid], Imidinyl™ [INCI: Tamarindus Indica Seed Polysaccharide], Phystrogene™ [INCI: Butylene Glycol, Malva Sylvestris (Mallow) Extract, Xanthan Gum] or Purisoft™ [INCI: Moringa Pterogysperma Seed Extract] marketed by Laboratoires Serobiologiques/Cognis/BASF; AquaCacteen™ [INCI: Glycerin, Opuntia Ficus Indica Stem Extract, Phenoxyethanol, Aqua], Trimoist™ (KMF) [INCI: Sodium Stearoyl Lactylate, Letyl alcohol, Vegetable oil, Tocopheryl acetate, Glycerin, *Glycine soja* sterol, Sodium lactate, Sodium carboxymethyl betaglucan, Carnosine], MelanoBronze™ [INCI: Vitex Agnus Castus Extract (Monk's pepper berries extract (phyto-endorphins)), Acetyl Tyrosine], CM-Glucan [INCI: Sodium Carboxymethyl Betaglucan, Phenoxyethanol, SunActin™ [INCI: Helianthus Annuus (Sunflower) Sprout Extract, Tocopherols, Glycerin, Lecithin, Phenoxyethanol, Aqua], GSP-T™ skin [INCI: Glycerin, Alcohol, Aqua, PEG-40 Hydrogenated Castor Oil, Vitis Vinifera (Grape) Seed Extract] or Detoxophane™ [INCI: Lepidium Sativum Sprout Extract, Lecithin, Phenoxyethanol, Glycerin, Water] marketed by Mibelle Biochemistry; Bacocalmine™ [INCI: PEG-8, Bacopa Monniera Extract, Water (Aqua), Hydroxyethylcellulose], Kombuchka™ [INCI: *Saccharomyces/Xylinum* Black Tea Ferment, Glycerin, Hydroxyethyl cellulose] or Prodizia™ [INCI: Albizia Julibrissin Extract, Glycerin] marketed by Sederma/Croda; Extramel™ C [INCI: Hydroxypropyltrimonium Maltodextrin Crosspolymer, Cucumis Melo (Melon) Fruit Extract] marketed by Seppic; Defensine™ [INCI: Triticum Vulgare Germ Extract] or Antiglyskin™ [INCI: Aqua, Helianthus Annuus Seed Extract] marketed by Silab; ATP™ 23 [INCI: Azeloyl Tetrapeptide-23] marketed by Sinergia; Glycofilm™ [INCI: Biosaccharide Gum-4] marketed by Solabia.

Applications

The invention extends to the use of a compound of general formula (I) as has been defined above, its stereoisomers, mixtures thereof and/or its cosmetically acceptable salts for the treatment of the skin, hair, nails and/or mucous membranes.

In a third aspect, the invention relates to the use of a compound of general formula (I) as has been defined above, its stereoisomers, mixtures thereof and/or its cosmetically acceptable salts for the cosmetic, non-therapeutic treatment and/or care of the skin, hair, nails and/or mucous membranes.

It has been found that the compound of the invention can increase the expression level of SOX2, OCT4, KLF4 and decrease the expression level of MYC in human epidermal keratinocytes; can decrease the expression level of Keratin 10 and increase the expression level of Keratin 14 in human epidermal keratinocytes; and can increase the pool of epidermal stem cells in reconstructed human epidermal tissue. The compound of the invention can be used to recover the germinative power of keratinocytes. The compound of the invention is useful in the cosmetic treatment and/or care of the skin, including: the treatment and prevention of the aging or the photoaging of the skin; the treatment or prevention of skin wrinkles; the improvement or maintenance of skin firmness; the protection of the skin from photo-ionizing radiation or exposure to the sun; rejuvenation of the skin; promoting the self-renewal properties of the skin; treatment of the loss of adipose tissue beneath the skin prevention or reduction of hypertrophic scarring of the skin.

In one embodiment of the invention, the treatment and/or care is of the skin. In this embodiment, the skin can be the skin of the face, neck, hands and décolletage.

In one embodiment of the third aspect of the invention, there is provided the cosmetic non-therapeutic use of the compound of the invention for the treatment and/or prevention of the aging or photoaging of the skin. This embodiment of the invention provides the cosmetic, non-therapeutic use of the compound of the invention for the alleviation and/or the prevention of symptoms of skin aging or skin photoaging. Thus, the invention provides for the use of the compound of the invention as a skin anti-aging and/or skin anti-photoaging agent. The symptoms of skin aging include the appearance of wrinkles, the loss of skin firmness, the loss of subcutaneous adipose tissue.

In one embodiment, there is provided the cosmetic non-therapeutic use of the compound of the invention for the treatment and/or prevention of skin wrinkles. Thus, the invention provides for the use of the compound of the invention as a skin anti-wrinkle agent.

In one embodiment, there is provided the cosmetic non-therapeutic use of the compound of the invention for the treatment and/or prevention of loss of subcutaneous adipose tissue. It is believed that the compound of the invention is effective in the treatment and/or prevention of loss of subcutaneous adipose tissue because it can stimulate lipid accumulation. In particular, this use can be for the skin the face, neck, hands and décolletage. The skin of the face includes the skin around the eye area.

In one embodiment, there is provided the cosmetic non-therapeutic use of the compound of the invention in rejuvenating the skin. It has been found that the compounds of the invention can promote regeneration of the skin. In this way, the compound of the invention can, for example, alleviate, prevent and/or delay the onset of the symptoms of aging. Thus, the invention provides for the use of the compound of the invention as a skin rejuvenating agent.

In one embodiment, there is provided the cosmetic non-therapeutic use of the compound of the invention in promoting the self-renewal properties of the skin. It has been found that the compounds of the can promote the self-renewing properties of the skin. In this way, the compound of the invention can, for example, alleviate, prevent and/or delay the onset of the symptoms of aging. Thus, the invention provides for the use of the compound of the invention as an agent for promoting the self-renewing properties of the skin.

In one embodiment of the second aspect of the invention, there is provided the cosmetic non-therapeutic use of the compound of the invention for the prevention or reduction of hypertrophic scarring of the skin.

The invention further provides for the use of a compound of the invention to reactivate the pool of epidermal stem cells in skin.

The invention further provides for the use of a compound of the invention to recover the germinative power of keratinocytes, or recover the properties of keratinocytes, in skin.

In a third aspect, the invention relates to a compound of general formula (I) as has been defined above, its stereoisomers, and/or its pharmaceutically acceptable salts for use as a medicament.

In one embodiment of the third aspect, the invention relates to a compound of general formula (I) as has been defined above its stereoisomers, and/or its pharmaceutically acceptable salts for use in the treatment of wounds. In particular, the compounds of the invention are useful in promoting or helping the healing of wounds.

In a fourth aspect, the invention relates to a cosmetic method of treatment and/or care of the skin, hair, nails or mucous membranes which comprises the administration of a cosmetically effective quantity of the compound of the invention to the skin, hair, nails or mucous membranes. In particular, the invention relates to a cosmetic method of treatment and/or care of the skin. In one embodiment, the administration is topical. In one embodiment the administration is transdermal. In this aspect of the invention, the compound of the invention may be present in a cosmetic composition, for example the cosmetic compositions described herein. Thus, the invention provides a cosmetic method of treatment and/or care of the skin, hair, nails or mucous membranes which comprises the administration of a cosmetic composition comprising a cosmetically effective quantity of the compound of the invention to the skin, hair, nails or mucous membranes of an individual.

In a fifth aspect, the invention relates to a method of treating or preventing a disease or disorder in a subject comprising administering a therapeutically effective amount of a compound of the invention or a pharmaceutical composition comprising a therapeutically effective amount of the compound, to the patient. In particular, the invention provides for a method of treating a wound comprising administering a therapeutically effective amount of a compound of the invention to the wound/skin around the wound. In one embodiment, the administration is topical. In one embodiment the administration is transdermal. In this aspect of the invention, the compound of the invention may be present in a pharmaceutical composition, for example the pharmaceutical compositions described herein. Thus, the invention provides a method of treating or preventing a disease or disorder in a subject comprising administering a therapeutically effective amount of the compound of the invention or a pharmaceutical composition comprising a therapeutically effective amount of the compound, to the patient.

For both the fourth and fifth aspects of the invention, topical or transdermal application can be carried out by iontophoresis, sonophoresis, electroporation, mechanical pressure, osmotic pressure gradient, occlusive cure, microinjections, by needle-free injections by means of pressure, by microelectric patches, face masks or any combination thereof.

For both the fourth and fifth aspects of the invention, the frequency of application or administration can vary greatly, depending on the needs of each subject, with a recommendation of an application from once a month to ten times a day, preferably from once a week to four times a day, more preferably from three times a week to twice a day, even more preferably once a day.

The invention is illustrated by the following non-limiting examples.

EXAMPLES

General Methodology

All reagents and solvents are of synthesis quality and are used without additional treatment.

ABBREVIATIONS

The abbreviations used for amino acids follow the 1983 IUPAC-IUB Joint Commission on Biochemical Nomenclature recommendations outlined in *Eur. J. Biochem.* (1984) 138:9-37.

®, resin; 2-ClTrt-®, 2-chlorotrityl resin; Ac, acetyl; AcOH, acetic acid; Ala, alanine; AM, 2-[4-aminomethyl-(2,4-dimethoxyphenyl)] phenoxyacetic acid; Arg, arginine; Asn, asparagine; Asp, aspartic acid; Boc, tert-butyloxycarbonyl; DCM, dichloromethane; DIEA, N,N'-diisopropylethylamine; DIPCDI, N,N'-diisopropylcarbodiimide; DMF, N,N-dimethylformamide; ESI-MS, electrospray ionization mass spectrometry; Fmoc, 9-flluorenylmethyloxycarbonyl; Gln, glutamine; Glu, glutamic acid; HOBt, 1-hydroxybenzotriazole; HPLC, high performance liquid chromatography; Ile, isoleucine; KOH, potassium hydroxide; Leu, leucine; Lys, lysine; MBHA, p-methylbenzhydrylamine; MeCN, acetonitrile; MeOH, methanol; Met, methionine; Myr, myristoyl; Orn, ornithine; Palm, palmitoyl; Pbf, 2,2,4,6,7-pentamethyldihydrobenzofurane-5-sulfonyl; Ser, serine; tBu, tert-butyl; TFA, trifluoroacetic acid; Thr, threonine; Trt, triphenylmethyl or trityl; Tyr, tyrosine; Val, Valine.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2:8, v/v) (1×1 min, 1×5 min, 5 mL/g resin) [Lloyd-Williams, P., et al. (1997) "*Chemical Approaches to the Synthesis of Peptides and Proteins*" CRC, Boca Raton (FL, USA)]. Washes between stages of deprotection, coupling, and, again, deprotection, were carried out with DMF (3×1 min) each time using 10 mL solvent/g resin. Coupling reactions were performed with 3 mL solvent/g resin. The control of the couplings was performed by carrying out the ninhydrin test [Kaiser, E., et al., *Anal. Biochem.*, (1970), 34: 595-598] or chloranil test [Christensen, T., *Acta Chem. Scand.*, (1979), 338, 763-766]. All synthetic reactions and washes were carried out at 25° C.

HPLC chromatographic analysis was carried out with Shimadzu equipment (Kyoto, Japan) using a reversed-phase column thermostatized at 30° C. (250×4.0 mm, Kromasil C$_8$, 5 µm, Akzo Nobel, Sweden). The elution was carried out using a gradient of acetonitrile (+0.07% TFA) in water (+0.1% TFA) at a flow rate of 1 mL/min and detection was carried out at 220 nm. The electrospray ionization mass spectrometry was carried out in a WATERS Alliance ZQ 2000 detector using a mixture of MeCN:H$_2$O 4:1 (+0.1% TFA) as the mobile phase and a flow rate of 0.3 mL/min.

Example 1

Obtaining Fmoc-W$_n$—X$_m$-AA$_1$-AA$_2$-AA$_3$-AA$_4$-AA$_5$-AA$_6$-Y$_p$—Z$_q$—O-2-ClTrt-®, wherein AA$_1$ is -L-Asn-, -L-Asp-, -L-Gln- or -L-Glu-; AA$_2$ is -L-Asp-, -L-Gln- or -L-Glu-; AA$_3$ is -L-Ile-, -L-Leu- or -L-Met-; AA$_4$ is -L-Arg-, -L-Lys- or -L-Orn-; AA$_5$ is -L-Leu-, -L-Met-, or -L-Val-; AA$_6$ is -L-Asn-, -L-Gln- or -L-Glu-; and n, m, p and q are 0.

8.59 g Fmoc-L-Asn(Trt)-OH, 8.79 g Fmoc-L-Gln(Trt)-OH or 6.39 g Fmoc-L-Glu(tBu)-OH (14.4 mmol; 1 equiv) dissolved in 90 mL of DCM to which was added 2.1 mL of DIEA (12.0 mmol; 0.83 equiv) were coupled onto the dry 2-chlorotrityl resin (9.0 g; 14.4 mmol). They were stirred for 5 min, after which 4.1 mL of DIEA were added (23.9 mmol; 1.66 equiv). The mixture was allowed to react for 40 min. The remaining chloride groups were blocked by treatment with 7.0 mL of MeOH.

The N-terminal Fmoc group was deprotected as described in the general methods and 12.72 g of Fmoc-L-Leu-OH, 13.37 g of Fmoc-L-Met-OH or 12.22 g of Fmoc-L-Val-OH (36 mmol; 2.5 equiv) were coupled onto the peptidyl resins in the presence of DIPCDI (6.09 mL, 39.6 mmol, 2.75 equiv) and HOBt (5.51 g, 36 mmol, 2.5 equiv) using DMF as a solvent for 1 hour. The resins were then washed as described in the general methods and the deprotection treatment of the Fmoc-group was repeated to couple the next amino acid. Following the protocols described 23.36 g of Fmoc-L-Arg(Pbf)-OH, 16.87 g of Fmoc-L-Lys(Boc)-OH or 16.36 g of Fmoc-L-Orn(Boc)-OH (36 mmol, 2.5 equiv); 12.72 g of Fmoc-L-Ile-OH, 12.72 g of Fmoc-L-Leu-OH or 13.37 g of Fmoc-L-Met-OH (36 mmol, 2.5 equiv); 14.81 g of Fmoc-L-Asp(tBu)-OH, 21.98 g of Fmoc-L-Gln(Trt)-OH or 15.97 g of Fmoc-L-Glu(tBu)-OH (36 mmol, 2.5 equiv) and subsequently 21.48 g of Fmoc-L-Asn(Trt)-OH, 14.81 g of Fmoc-L-Asp(tBu)-OH, 21.98 g of Fmoc-L-Gln(Trt)-OH or 15.97 g of Fmoc-L-Glu(tBu)-OH (36 mmol, 2.5 equiv) were sequentially coupled in the presence of 5.51 g of HOBt (36 mmol, 2.5 equiv) and 6.09 mL of DIPCDI (39.6 mmol; 2.75 equiv) in each coupling.

Example 2

Obtaining Fmoc-W$_n$—X$_m$-AA$_1$-AA$_2$-AA$_3$-AA$_4$-AA$_5$-AA$_6$-Y$_p$—Z$_q$-AM-MBHA-®, wherein AA$_1$ is -L-Gln-; AA$_2$ is -L-Asp- or -L-Glu-; AA$_3$ is -L-Ile- or -L-Met-; AA$_4$ is -L-Arg-; AA$_5$ is -L-Ile-, -L-Leu- or -L-Met-; AA$_6$ is -L-Asn- or -L-Gln-; and n, m, p and q are 0.

590 mg of Fmoc-AM-MBNA resin with a functionalization of 0.52 mmol/g (0.3 mmol) were treated with piperidine:DMF according to the described general protocol in order to remove the Fmoc group. 895 mg of Fmoc-L-Asn (Trt)-OH or 928 mg of Fmoc-L-Gln(Trt)-OH (1.5 mmol; 5 equiv) were incorporated onto the deprotected resin in the presence of DIPCDI (257 µL, 1.65 mmol; 5.5 equiv) and HOBt (233 mg; 1.5 mmol; 5 equiv) using DMF as a solvent for 1 hour.

The resins were then washed as described in the general methods and the deprotection treatment of the Fmoc group was repeated to couple the next amino acid. Following the previously described protocols 530 mg of Fmoc-L-Ile-OH, 530 mg of Fmoc-L-Leu-OH or 565 mg of Fmoc-L-Met-OH (1.5 mmol, 5 equiv); 986 mg of Fmoc-L-Arg(Pbf)-OH (1.5 mmol, 5 equiv); 530 mg of Fmoc-L-Ile-OH or 565 mg of Fmoc-L-Met-OH (1.5 mmol, 5 equiv); 617 mg of Fmoc-L-Asp(tBu)-OH or 674 mg of Fmoc-L-Glu(tBu)-OH (1.5 mmol, 5 equiv) and subsequently 928 mg of Fmoc-L-Gln (Trt)-OH (1.5 mmol, 5 equiv) were sequentially coupled in the presence of 233 mg of HOBt (1.5 mmol, 5 equiv) and 257 µL of DIPCDI (1.65 mmol; 5.5 equiv) in each coupling.

After the synthesis, the peptidyl resins were washed with DCM (3×1 min).

Example 3

General Process for Removal of Fmoc N-Terminal Protective Group.

The N-terminal Fmoc group of the peptidyl resins obtained in examples 1 and 2 was deprotected as described in the general methods (20% piperidine in DMF, 1×1 min+1×5 min). The peptidyl resins were washed with DMF (5×1 min), DCM (3×1 min), diethyl ether (3×1 min) and dried under vacuum.

Example 4

Process for Introducing the R$_1$ Palmitoyl Group onto the Peptidyl Resins Obtained in Example 3.

197 mg of palmitic acid (770 µmol, 5 equiv) pre-dissolved in DMF (1 mL) were added onto 154 µmol of the peptidyl resins obtained in Example 3, in the presence of 118 mg of HOBt (770 µmol, 5 equiv) and 130 µL of DIPCDI (874 µmol, 5.5 equiv). They were allowed to react for 3 hours, after which the resins were washed with DMF (10×1 min), DCM (4×1 min), ether (3×1 min) and were dried under vacuum.

Example 5

Process for Introducing the R$_1$ Myristoyl Group onto the Peptidyl Resins Obtained in Example 3.

167 mg of myristic acid (0.75 mmol; 5 equiv) pre-dissolved in DMF (1 mL) were added onto 0.15 mmol of the peptidyl resins obtained in Example 3, in the presence of 112 mg of HOBt (0.75 mmol; 5 equiv) and 124 µL of DIPCDI (0.82 mmol; 5.5 equiv). They were allowed to react for 3 hours, after which the resins were washed with DMF (3×1 min), DCM (3×1 min), ether (3×1 min) and were dried under vacuum.

Example 6

Process for Introducing the R$_1$ Acetyl Group onto the Peptidyl Resins Obtained in Example 3.

0.15 mmol of the peptidyl resins obtained in Example 3 was treated with 25 equiv of acetic anhydride in the presence of 25 equiv of DIEA using 2 mL of DMF as a solvent. They were allowed to react for 30 min, after which the resins were washed with DMF (3×1 min), DCM (3×1 min), ether (3×1 min) and were dried under vacuum.

Example 7

Cleavage Process from the Polymeric Support of the Peptidyl Resins Obtained in Examples 3, 4, 5 and 6.

257 mg of the dried peptidyl resins obtained in Examples 3, 4, 5 and 6 were treated with 1.8 mL of TFA:$H_2O$ (95:5) for 2 hours at room temperature under stirring. The filtrates were collected onto 18 mL of cold diethyl ether, then they were filtered through polypropylene syringes fitted with porous polyethylene discs and washed 5 times with 10 mL diethyl ether. The final precipitates were dried under vacuum.

HPLC analysis of the obtained peptides in gradients of MeCN (+0.07% TFA) in $H_2O$ (+0.1% TFA) showed a purity exceeding 85% in all cases. The identity of the peptides obtained was confirmed by ESI-MS.

Example 8

Cleavage process from the polymeric support and functionalization with $R_2$ substituted amine: Obtaining Ac—$W_n$—$X_m$-$AA_1$-$AA_2$-$AA_3$-$AA_4$-$AA_5$-$AA_6$-$Y_p$—$Z_q$—NH—$(CH_2)_5$—$CH_3$, wherein $AA_1$ is -L-Gln-; $AA_2$ is -L-Asp-, or -L-Glu-; $AA_3$ is -L-Met-; $AA_4$ is -L-Arg; $AA_5$ is -L-Met-; $AA_6$ is -L-Gln-; and n, m, p and q are 0.

The peptides Ac—$W_n$—$X_m$-$AA_1$-$AA_2$-$AA_3$-$AA_4$-$AA_5$-$AA_6$-$Y_p$—$Z_q$—OH with fully protected side chains were obtained by treating 325 mg of the peptidyl resins Ac—$W_n$—$X_m$-$AA_1$-$AA_2$-$AA_3$-$AA_4$-$AA_5$-$AA_6$-$Y_p$—$Z_q$—O-2-ClTrt-® of Example 6, previously desiccated under vacuum in the presence of KOH, with 2.3 mL AcOH for 2 hours. The filtrates were collected and the resins were washed with 4 mL AcOH (1×1 min) and 5 mL of 50% AcOH in $H_2O$ (1×1 min). The filtrates together with the ones obtained in the washing steps were combined and lyophilized.

171 mg of the obtained crude peptides were weighed in a flask and 3 equiv of hexylamine.HOBt and 8 mL of anhydrous DMF were added. 2 equiv of DIPCDI were added, and left to react being magnetically stirred at 47° C. The reactions were monitored by HPLC until disappearance of the initial products, which were complete after 2-4 hours. Solvents were evaporated to dryness and co-evaporated twice with DCM. The obtained residues were dissolved in 13 mL of a mixture of TFA:$H_2O$ (95:5) and left to react for 2 hours at room temperature. 130 mL of cold diethyl ether were added, the solvents were evaporated under reduced pressure and two additional co-evaporations with ether were carried out. The residues were dissolved in a mixture of 50% MeCN in $H_2O$ and lyophilized.

HPLC analysis of the obtained peptides in gradients of MeCN (+0.07% TFA) in $H_2O$ (+0.1% TFA) showed a purity exceeding 85% in all cases. The identity of the peptides obtained was confirmed by ESI-MS.

Example 9: Study of the Modulation of Stem Cell Markers in Human Epidermal Keratinocytes from Adult (HEKa) Using Real Time PCR Arrays The candidate compound is evaluated for the modulation of several stem cell markers, those transcription factors regulated by miRNA145 (SOX2, OCT4, KLF4 and MYC). Gene expression profiles are analyzed by Real Time PCR Arrays using a 96-well panel for use with SYBR® Green (BioRad) to detect mRNA expression levels of stem cell markers plus three housekeeping genes, and five controls, in Human Epidermal Keratinocytes from adult (HEKa) (Cascade Biologics).

HEKa cells are seeded at 6.0×10$^5$ cells/well in 6-well plates and incubated in culture medium, Epilife with defined Growth Supplement (EDGS) (Cascade Biologics), for 24 hours at 37° C. in a water-saturated atmosphere of 95% air and 5% $CO_2$. After 24 hours, the medium is removed and the cells are incubated with the synthetic peptide DD14024 at several concentrations in a culture medium. Cells are incubated with culture medium only and these provide the basal conditions. After 48 hours of treatment at 37° C. in a $CO_2$ incubator, the cells are lysed directly in the wells, and RNA is purified following the protocol described on the RNeasy Mini kit (Qiagen) according to the manufacturer's protocol. After RNA elution, quantification and analysis of purity of RNA samples are performed with a biophotometer (Eppendorf). For each sample, 2 μg of high quality RNA is retrotranscribed with iScript Advanced (BioRad) in a final volume of 20 μl. The complete reaction mix is incubated in a thermal cycler (Eppendorf) at 42° C. for 30 minutes and the reaction is stopped at 85° C. for 5 minutes (?). Complementary DNA is amplified by qPCR in a real-time PCR thermocycler (BioRad) using SYBR Green Supermix (BioRad) in the 96-well panel for use with SYBR® Green (BioRad). SYBR Green binds to double-stranded DNA molecules and emits fluorescence which is quantified; the fluorescence intensity is proportional to the amount of the product in the PCR reaction. Cycling conditions in BioRad CFX96 instrument are: 95° C. for 3 minutes, followed by 40 cycles of denaturing at 95° C. for 5 seconds, annealing and elongation at 60° C. for 30 seconds. GAPDH, TBP and HRPT1 are used as endogenous controls. Fold change relative to the expression of the sample genes and reference genes is calculated using normalized expression ($\Delta\Delta(Ct)$) method using CFX Manager Software (BioRad). The results are presented in Tables 3 to 6. Each result represents the mean value obtained in 3 or in 4 independent experiments.

TABLE 3

| Gene name | Treatment | Dose tested | Fold induction respect to basal conditions |
|---|---|---|---|
| SOX2 | DD14024 | 0.001 mg/ml | 1.62 ± 0.18 |
| SOX2 | DD14024 | 0.005 mg/ml | 3.00 ± 0.55 |
| SOX2 | DD14024 | 0.01 mg/ml | 2.81 ± 0.26 |

TABLE 4

| Gene name | Treatment | Dose tested | Fold induction respect to basal conditions |
|---|---|---|---|
| OCT4 | DD14024 | 0.001 mg/ml | 1.65 ± 0.13 |
| OCT4 | DD14024 | 0.005 mg/ml | 1.81 ± 0.28 |
| OCT4 | DD14024 | 0.01 mg/ml | 1.71 ± 0.29 |

TABLE 5

| Gene name | Treatment | Dose tested | Fold induction respect to basal conditions |
|---|---|---|---|
| KLF4 | DD14024 | 0.001 mg/ml | 1.66 ± 0.18 |
| KLF4 | DD14024 | 0.005 mg/ml | 2.42 ± 0.50 |
| KLF4 | DD14024 | 0.01 mg/ml | 1.71 ± 0.40 |

TABLE 6

| Gene name | Treatment | Dose tested | Fold induction respect to basal conditions |
|---|---|---|---|
| MYC | DD14024 | 0.001 mg/ml | 0.91 ± 0.05 |
| MYC | DD14024 | 0.005 mg/ml | 0.65 ± 0.08 |
| MYC | DD14024 | 0.01 mg/ml | 0.65 ± 0.07 |

The results show that the synthetic peptide candidate is able to increase the expression level of SOX2, OCT4, KLF4 and decrease the expression level of MYC, respect to basal conditions in HEKa at the tested concentrations.

Example 10: Study of the Keratins Expression Profile in Human Epidermal Keratinocytes from Adult (HEKa) Using Real Time PCR Arrays The candidate compound is assayed for its ability to recover the basal keratinocyte state. The keratinocytes of the four layers of the epidermis present different expression patterns of keratins. Basal keratinocytes strongly express Keratin 14 and when differentiated, Keratin 10 is increased. To elucidate the keratinocyte state (basal or differentiated), the expression profile of keratins is analyzed by Real Time PCR Arrays, using a 96-well panel for use with SYBR® Green (BioRad) to detect mRNA expression levels of two keratin genes (Keratins 10 and 14) plus three housekeeping genes, and five controls, in Human Epidermal Keratinocytes from adult (HEKa) (Cascade Biologics).

HEKa cells are seeded at $6.0 \times 10^5$ cells/well in 6-well plates and incubated in culture medium Epilife with defined Growth Supplement (EDGS) (Cascade Biologics), for 24 hours at 37° C. in a water-saturated atmosphere of 95% air and 5% $CO_2$. After 24 hours, the medium is removed and the cells are incubated with the synthetic peptide candidate at several concentrations in culture medium that contains 1 mM $CaCl_2$) (Sigma) to induce differentiation of keratinocytes. Cells are incubated with 1 mM $CaCl_2$) in culture medium and this provides a positive control of differentiation. Cells are incubated with culture medium only and these provide basal conditions. After 48 hours of treatment at 37° C. in a $CO_2$ incubator, the cells are lysed directly in the wells, and RNA is purified following the protocol described on the RNeasy Mini kit (Qiagen) according to the manufacture's protocol. After RNA elution, quantification and analysis of purity of RNA samples are performed with a biophotometer (Eppendorf). For each sample, 2 μg of high quality RNA is retrotranscribed with iScript Advanced (BioRad) in a final volume of 20 μl. The complete reaction mix is incubated in a thermal cycler (Eppendorf) at 42° C. for 30 minutes and the reaction is stopped at 85° C. for 5 minutes. Complementary DNA is amplified by qPCR in a real-time PCR thermocycler (BioRad) using SYBR Green Supermix (BioRad) in the 96-well panel for use with SYBR® Green (BioRad). SYBR Green binds to double-stranded DNA molecules and emits fluorescence which is quantified; the fluorescence intensity is proportional to the amount of the product in the PCR reaction. Cycling conditions in BioRad CFX96 instrument are: 95° C. for 3 minutes, followed by 40 cycles of denaturing at 95° C. for 5 seconds, annealing and elongation at 60° C. for 30 seconds. GAPDH, TBP and HRPT1 are used as endogenous controls. Fold change relative to the expression of the sample genes and reference genes is calculated using normalized expression (ΔΔ(Ct)) method using CFX Manager Software (BioRad).

The results are presented in Tables 7 and 8. Each result represents the mean value obtained in 3 to 8 independent experiments.

TABLE 7

| Gene name | Treatment | Dose tested | Fold induction respect to positive control of differentiation |
|---|---|---|---|
| Keratin 10 | DD14024 | 0.001 mg/ml | 0.68 ± 0.04 |
| Keratin 10 | DD14024 | 0.005 mg/ml | 0.60 ± 0.02 |
| Keratin 10 | DD14024 | 0.01 mg/ml | 0.72 ± 0.06 |

TABLE 8

| Gene name | Treatment | Dose tested | Fold induction respect to positive control of differentiation |
|---|---|---|---|
| Keratin 14 | DD14024 | 0.001 mg/ml | 1.29 ± 0.15 |
| Keratin 14 | DD14024 | 0.005 mg/ml | 1.36 ± 0.15 |
| Keratin 14 | DD14024 | 0.01 mg/ml | 1.30 ± 0.09 |

The results show that the synthetic peptide candidate is able to decrease the expression level of Keratin 10 and increase the expression level of Keratin 14, respect to positive control of differentiation (1 mM $CaCl_2$ in culture medium) in HEKa at the tested conditions.

Example 11: In Vitro Study of miRNA145 Inhibition on Human Keratinocyte HaCaT Cell Line Using a Direct miRNA145 Quantification Assay Based on Luminescence Detection The synthetic peptide candidates are evaluated for the inhibition of human miRNA145 expression level using a direct miRNA145 quantification assay based on luminescence detection in a Human Keratinocyte HaCaT cell line.

HaCat cells (Deutsches Krebsforschungszentrum) are seeded at $3.0 \times 10^4$ cells/well in 96-clear wells plates and incubated in a culture medium [(DMEM High Glucose with L-Glutamine (Lonza), supplemented with 10% Fetal Bovine Serum (Cultek)] for 24 hours at 37° C. in a water-saturated atmosphere of 95% air and 5% $CO_2$. Then, the cells with the candidates added at 0.3 mg/ml in the culture medium are treated for 24 hours at 37° C., 95% air and 5% $CO_2$. Cells with culture medium only are treated to the same conditions to provide basal conditions. Each cell culture condition is assayed at least in 6 biological replicates. At the end of the incubation period, the cells are lysed and the relative miRNA145 expression level is quantified by a specific assay kit (QuantiGene™ 2.0 miRNA Assay Kit) following manufacturer's instructions (Affymetrix). Briefly, to capture miRNA145, culture lysates are incubated overnight at 46±1° C. in 96-white well plates with the miRNA145 specific probe set (Capture extenders and Label extenders). As an endogenous expression control, the housekeeping Snord48 is quantified using a specific probe set. Next day, the signal amplification tree is built via sequential hybridization at 46±1° C. of three probes: PreAmplifier, Amplifier and Alkaline Phosphatase Label Probe. Then, the signal is detected by adding a chemiluminescent substrate and using a Microplate Luminometer Reader (Clariostar-BMG LabTech).

The miRNA145 expression level result is normalized with the Snord48 expression level for each cell culture condition and the relative decrease in the miRNA145 expression level is calculated respect to basal control (cells treated with culture medium only). The results are presented in Table 9. The values represent the mean of 3 independent experiments for DD14024, and for the other candidates, represent the result of one experiment.

TABLE 9

| Treatment | Sequence | Relative level of miRNA145 respect to basal control (%) |
|---|---|---|
| DD14024 | Ac-Gln-Glu-Met-Arg-Met-Gln-OH | 85.06 ± 6.35 |
| DD15002 | H-Gln-Glu-Met-Arg-Met-Gln-OH | 89.75 ± 0.69 |
| DD15003 | Palm-Gln-Glu-Met-Arg-Met-Gln-OH | 76.38 ± 7.00 |
| DD14023 | Ac-Gln-Glu-Met-Arg-Met-Gln-NH$_2$ | 87.03 ± 2.65 |
| DD15004 | Ac-Gln-Glu-Met-Arg-Met-Gln-NHC$_6$H$_{13}$ | 89.03 ± 5.37 |
| DD15052 | Myr-Gln-Glu-Met-Arg-Met-Gln-NH$_2$ | 92.94 ± 1.35 |
| DD15012 | Ac-Asp-Glu-Met-Arg-Met-Gln-OH | 71.05 ± 3.82 |
| DD15051 | Ac-Glu-Glu-Met-Arg-Met-Gln-OH | 92.26 ± 1.61 |
| DD15014 | Ac-Gln-Gln-Met-Arg-Met-Gln-OH | 80.06 ± 3.47 |
| DD15017 | Ac-Gln-Glu-Met-Lys-Met-Gln-OH | 85.50 ± 1.74 |
| DD15022 | Ac-Gln-Glu-Met-Orn-Met-Gln-OH | 75.41 ± 2.25 |
| DD15020 | Ac-Gln-Glu-Met-Arg-Met-Glu-OH | 62.43 ± 0.89 |
| DD15056 | Ac-Gln-Glu-Met-Arg-Met-Asn-OH | 72.43 ± 1.39 |
| DD15011 | Myr-Glu-Glu-Met-Arg-Met-Gln-OH | 73.29 ± 4.37 |
| DD15013 | Ac-Gln-Asp-Met-Arg-Met-Gln-NHC$_6$H$_{13}$ | 84.32 ± 6.96 |
| DD15015 | Palm-Gln-Glu-Leu-Arg-Met-Gln-OH | 14.07 ± 0.28 |
| DD15016 | H-Gln-Glu-Ile-Arg-Met-Gln-NH$_2$ | 87.63 ± 4.46 |
| DD15019 | H-Gln-Glu-Met-Arg-Ile-Gln-NH$_2$ | 67.00 ± 2.89 |
| DD15055 | H-Gln-Glu-Met-Arg-Leu-Gln-NH$_2$ | 67.03 ± 0.23 |
| DD15023 | Ac-Glu-Glu-Ile-Arg-Met-Gln-NHC$_{16}$H$_{33}$ | 74.48 ± 3.34 |
| DD15053 | Ac-Asp-Gln-Met-Arg-Met-Gln-OH | 58.64 ± 0.04 |
| DD15054 | Ac-Glu-Gln-Met-Arg-Met-Gln-OH | 72.50 ± 2.88 |
| DD15024 | Ac-Gln-Glu-Met-Lys-Leu-Gln-OH | 87.92 ± 1.32 |
| DD15025 | H-Gln-Asp-Met-Arg-Met-Asn-NH$_2$ | 86.95 ± 0.55 |
| DD15026 | Ac-Asn-Glu-Ile-Arg-Val-Gln-OH | 77.60 ± 5.43 |
| DD15027 | Ac-Gln-Asp-Met-Lys-Met-Asn-OH | 78.47 ± 0.74 |
| DD15045 | Ac-Pro-Gln-Glu-Met-Arg-Met-Gln-OH | 90.71 ± 4.78 |
| DD15046 | Ac-Gln-Glu-Met-Arg-Met-Gln-Tyr-OH | 74.02 ± 1.98 |
| DD15047 | Ac-Gln-Glu-Met-Arg-Met-Gln-Thr-NH$_2$ | 77.67 ± 9.10 |
| DD15048 | Ac-Pro-Val-Gln-Glu-Met-Arg-Met-Gln-OH | 89.54 ± 3.79 |
| DD15049 | Ac-Gln-Glu-Met-Arg-Met-Gln-Val-Tyr-OH | 80.09 ± 7.49 |
| DD15050 | Ac-Ser-Gln-Glu-Met-Arg-Met-Gln-Thr-NH$_2$ | 72.44 ± 3.87 |

The results show that the peptide candidates are able to decrease the relative miRNA145 expression level in a Human Keratinocyte HaCaT cell line at the tested conditions.

Example 12: Measuring the Activation of the Pool of Epidermal Stem Cell in Reconstructed Human Epidermal Tissue (RHE) In Vitro Using an Immunohistochemistry Assay The aim of this study is to measure the activation of the pool of epidermal stem cell in reconstructed human epidermal tissue (RHE) in vitro after treatment with the candidate peptide by measuring p63 using an immunohistochemistry assay. p63 is a specific keratinocyte stem cell marker that functions in maintaining the proliferative potential of the keratinocyte stem cells, and is expressed in the nuclei of cells that are either proliferating or possess the ability to multiply. Therefore, an increase in the expression of p63 would mean a higher regenerative potential compared to basal conditions.

The SkinEthic human tissue models (RHE) are removed from the agarose-nutrient solution in the multiwell plate immediately after arrival and are placed in a 6-well plate in which each well has previously be filled with SkinEthic Growth Medium (EPISKIN). After overnight incubation at 37° C., 5% $CO_2$, the medium is removed. Then, the tissue models are incubated with the candidate peptide at 10 µg/ml at 37° C. and 5% $CO_2$ for 24 hours. The tissue models are embedded in Tissue Teck OCT compound (Aname™). After 24 hours of treatment, the tissue models are fixed in 4% paraformaldehyde (Sigma) for 3 hours at 4° C. and are washed 4 times with phosphate-buffered saline (PBS) (Sigma). Then, samples are treated to a sucrose gradient from 0.6M to 2.3M with incubations of 3 hours at room temperature. After the last incubation, the tissue models are embedded in Tissue Teck OCT compound and frozen at −20° C. Frozen tissue sections of about 10 µm thickness are cut using a cryomicrotome (Leica, CM3050), collected on coated slides and finally stored at −20° C.

The expression of p63 is evaluated by immunohistochemistry with a specific primary antibody and a fluorescently labelled secondary antibody. Defrosted slides are fixed with frozen solution of acetone for 10 minutes at room temperature then are rinsed with PBS. Slides are permeabilized with 0.5% saponin for 10 minutes and then are rinsed with PBS. Non-specific sites are saturated with 1% BSA/0.1% Tween/300 mM Glycine for 30 minutes at room temperature. After rinsing with 1% BSA/0.1% Tween in Phosphate buffered saline (PBS), the slides are incubated with the primary antibody (Anti-p63 EPR5701 antibody (Abcam), diluted in 1% BSA/0.1% Tween in PBS) in a humidified chamber at room temperature for 2 hours. At the end of the incubation, slides are washed with PBS and are incubated with Alexa Fluor® 488 Goat anti-rabbit IgG (H+L) secondary antibody (Invitrogen, green fluorescence emission dye) 1 hour at room temperature in a dark humidified chamber. After rinsing with PBS, the sections are mounted in prolong Gold antifade reagent with Dapi (Invitrogen).

Microscopical observations are performed with a Zeiss fluorescence microscope and photographs of each condition are taken with the associated camera. From each fluorescence image of p63, values of the product of Mean Intensity and Area are quantified and normalized by control (basal condition, treated with SkinEthic Growth Medium). 6-20 representative images from each condition are collected and analyzed with the ZEN software (Zeiss). The values represent either the result from one experiment or the mean of four independent experiments.

TABLE 10

| Treatment | Dose tested | Fold induction respect to basal conditions |
|---|---|---|
| DD14024 (1 experiment) | 10 µg/ml | 1.63 ± 0.16 |
| DD14024 (mean of four experiments) | 10 µg/ml | 2.11 ± 0.23 |

The application of the candidate peptide increases the pool of epidermal stem cell in a RHE model.

Example 13: Recovering the Keratin Expression of Basal Keratinocytes in Reconstructed Human Epidermal Tissue (RHE) In Vitro Using an Immunohistochemistry Assay The human epidermis continuously renews itself by a process of proliferation and differentiation of keratinocytes. Basal epidermal stem cells proliferate and the differentiation process begins above the basal layer, whereby the differentiating keratinocytes slowly move outward from the basal membrane, migrate through the epidermis, and undergo terminal differentiation culminating in fully differentiated dead cells on the surface. The process is a dynamic flux so that surface cells are continuously sloughed and replaced by inner cells differentiating and moving outward. During the process of differentiation, the transition of keratinocytes from the proliferative basal cell layer to the suprabasal cell layers is characterized by a profound change in keratin expression. Basal keratinocytes strongly express Keratin 14 and when differentiated, Keratin 10 is increased. Ageing has a significant impact on the renewal processes in the epidermis, reducing the proliferation rate of the keratinocytes in the basal layer, and reducing also the effectiveness of the differentiation process. To study the ability of the peptides of the invention to recover the basal keratinocyte state, the expression of Keratins 10 and 14 is evaluated by immunohistochemistry in a three-dimensional culture system, Reconstructed Human Epidermal Tissue (RHE), that reproduces in vitro the histological organization of human epidermis in situ.

The SkinEthic human tissue models (EPISKIN™) are removed from the agarose-nutrient solution in the multiwell plate immediately after arrival and are placed in a 6-well plate in which each well has previously been filled with SkinEthic Growth Medium (EPISKIN). After overnight incubation at 37° C., 5% $CO_2$, medium is removed. Then, RHE are incubated with peptide DD14024 at 10 µg/ml at 37° C. and 5% $CO_2$ for 48 hours. All treatments are applied to two RHE per condition. After 48 hours of treatment, the tissue models are fixed in 4% paraformaldehyde (Sigma) for 3 hours at 4° C. and they are washed 4 times with phosphate-buffered saline (PBS, Sigma). Then, samples are treated with a sucrose gradient from 0.6 M to 2.3 M with incubations of 3 hours at room temperature. After the last incubation, the tissue models are embedded in Tissue Freezing Medium and frozen at −20° C. Frozen tissue sections of about 10 µm thickness are cut using a cryomicrotome (Leica, CM1950), collected on coated slides and finally stored at −20° C.

The expression of Keratins 10 and 14 is evaluated by immunohistochemistry with a specific primary antibody and a fluorescently labelled secondary antibody. Briefly, defrosted slides are fixed with frozen acetone (Quimivita™) for 10 minutes at room temperature and then are rinsed with PBS. Slides are permeabilized with 0.5% solution of saponin (Sigma) in PBS for 10 minutes and then are rinsed with further PBS. Non-specific sites are saturated with 10% normal goat serum (Life Technologies) in PBS for 30 minutes at room temperature. After rinsing with 0.2% solution of Tween 20 (Sigma) in PBS, the slides are incubated with the primary antibodies (either Anti-Keratin10 RKSE60 or Anti-Keratin14 RCK107, Abcam) diluted in 10% normal goat serum in PBS, in a humidified chamber and at room temperature for 2 hours. At the end of the incubation, slides are washed with 0.2% solution of Tween 20 in PBS and are incubated with Alexa Fluor® 488 Goat anti-mouse IgG (H+L) secondary antibody (Invitrogen, green fluorescence emission dye) for 1 hour at room temperature in a dark humidified chamber. After rinsing with PBS, the sections are mounted in Prolong® Gold Antifade Reagent with 4',6-diamino-2-fenilindol (Dapi, Invitrogen).

Microscopical observations are performed with a Zeiss fluorescence microscopy and photographs of each condition are taken with the associated camera. From each fluorescence image of Keratins 10 and 14, values of the product of Mean Intensity and Area are quantified and normalized by control (basal condition, treated only with SkinEthic Growth Medium). For both keratins, 10 to 24 representative images from each condition are collected and analyzed with the ZEN software (Zeiss). The value represents the mean of three independent experiments.

TABLE 11

| Keratin | Treatment | Dose tested | Fold induction respect to basal conditions (%) |
|---|---|---|---|
| Keratin 10 | DD14024 | 10 µg/ml | 28.70 |
| Keratin 14 | DD14024 | 10 µg/ml | 425.83 |

The results show that the application of the synthetic peptide candidate is able to decrease the Keratin 10 expression and increase the Keratin 14 expression with respect to basal condition and thus is capable of recovering the basal keratinocyte state in a RHE model.

Example 14

Preparation of a Cosmetic Composition (Cream) Containing Peptide DD14024

In a suitable vessel, the ingredients of phase A (water [INCI: WATER (AQUA)], Zemea™ [INCI: PROPANEDIOL], 1,2-dihydroxypentane [INCI: PENTYLENE GLYCOL], and disodium EDTA [INCI: DISODIUM EDTA]) are dissolved under rotor stirring.

Next, phase A1 (Carbopol® Ultrez 10 Polymer [INCI: CARBOMER]) is added and left to wet and disperse in the mixture. Phase A2 (Cola® Fax CPE-K [INCI: POTASSIUM CETYL PHOSPHATE]) is subsequently added and let to disperse too. The mixture is then heated at 70-75° C.

In a separate vessel, phase B ingredients (Schercemol™ DIA Ester [INCI: DIISOPROPYL ADIPATE], Phytocream® 2000 [INCI: GLYCERYL STEARATE, CETEARYL ALCOHOL, POTASSIUM PALMITOYL HYDROLYZED WHEAT PROTEIN], 2-ethylhexyl cocoate [INCI: ETHYLHEXYL COCOATE], polydimethylsiloxane [INCI: DIMETHICONE], vitamin E acetate [INCI: TOCOPHERYL ACETATE] and 2-phenoxyethanol [INCI: PHENOXYETHANOL]) are weighted and mixed, heating the resulting mixture at 70-75° C.

When both mixtures reach the corresponding temperatures, the emulsion is made by adding slowly phase B onto the mixture of phases A under stirring with turbine.

Once the mixture is cooled to 40° C., phase C (Novemer™ EC-1 polymer [INCI: MINERAL OIL (PARAFFINUM LIQUIDUM), WATER (AQUA), ACRYLATES/ACRYLAMIDE CROSSPOLYMER, POLYSORBATE 85]), followed by phase D (perfume [INCI: FRAGANCE (PARFUM)]) and by phase E (pre-mixture of water [INCI WATER (AQUA)], disodium phosphate [INCI: DISODIUM PHOSPHATE], peptide DD14024, sodium dihydrogen phosphate [INCI: SODIUM PHOSPHATE], and octane-1,2-diol [INCI: CAPRYLYL GLYCOL]) are sequentially added to the previous mixture.

Last, phase F (water [INCI: WATER (AQUA)] and sodium hydroxide [INCI: SODIUM HYDROXIDE]) is incorporated into the previous mixture for pH adjustment to 6.0-6.5.

The entire list of ingredients is presented in Table 12.

TABLE 12

| Phase | INGREDIENT (INCI name) | % weight |
|---|---|---|
| A | WATER (AQUA) | 66.1000 |
| A | PROPANEDIOL | 10.0000 |
| A | PENTYLENE GLYCOL | 2.0000 |
| A | DISODIUM EDTA | 0.2000 |
| A1 | CARBOMER | 0.5000 |
| A2 | POTASSIUM CETYL PHOSPHATE | 0.5000 |
| B | DIISOPROPYL ADIPATE | 5.0000 |
| B | [GLYCERYL STEARATE, CETEARYL ALCOHOL, POTASSIUM PALMITOYL HYDROLYZED WHEAT PROTEIN] | 5.0000 |
| B | ETHYLHEXYL COCOATE | 2.5000 |
| B | DIMETHICONE | 1.0000 |
| B | TOCOPHERYL ACETATE | 0.5000 |
| B | PHENOXYETHANOL | 0.5000 |
| C | [MINERAL OIL (PARAFFINUM LIQUIDUM), WATER (AQUA), ACRYLATES/ACRYLAMIDE CROSSPOLYMER, POLYSORBATE 85] | 1.0000 |
| D | FRAGANCE (PARFUM) | 0.2000 |
| E | WATER (AQUA) | 4.9345 |
| E | DISODIUM PHOSPHATE | 0.0413 |
| E | Peptide DD14024 | 0.0010 |
| E | SODIUM PHOSPHATE | 0.0132 |
| E | CAPRYLYL GLYCOL | 0.0100 |
| F | [WATER, SODIUM HYDROXIDE] | q.s. |

Example 15

Preparation of a Placebo Cosmetic Composition (Cream)

In a suitable vessel, the ingredients of phase A (water [INCI: WATER (AQUA)], Zemea™ [INCI: PROPANEDIOL], 1,2-dihydroxypentane [INCI: PENTYLENE GLYCOL]; and disodium EDTA [INCI: DISODIUM EDTA]) are dissolved under rotor stirring.

Next, phase A1 (Carbopol® Ultrez 10 Polymer [INCI: CARBOMER]) is added and left to wet and disperse in the mixture. Phase A2 (Cola® Fax CPE-K [INCI: POTASSIUM CETYL PHOSPHATE]) is subsequently added and left to disperse too. The mixture is then heated at 70-75° C.

In a separate vessel, phase B ingredients (Schercemol™ DIA Ester [INCI: DIISOPROPYL ADIPATE], Phytocream® 2000 [INCI: GLYCERYL STEARATE, CETEARYL ALCOHOL, POTASSIUM PALMITOYL HYDROLYZED WHEAT PROTEIN], 2-ethylhexyl cocoate [INCI: ETHYLHEXYL COCOATE], polydimethylsiloxane [INCI: DIMETHICONE], vitamin E acetate [INCI:

TOCOPHERYL ACETATE] and 2-phenoxyethanol [INCI: PHENOXYETHANOL]) are weighed and mixed, heating the resulting mixture at 70-75° C.

When both mixtures reach the corresponding temperatures, the emulsion is made by adding slowly phase B onto the mixture of phases A under stirring with turbine.

Once the mixture is cooled to 40° C., phase C (Novemer™ EC-1 polymer [INCI: MINERAL OIL (PARAFFINUM LIQUIDUM), WATER (AQUA), ACRYLATES/ACRYLAMIDE CROSSPOLYMER, POLYSORBATE 85]), followed by phase D (perfume [INCI: FRAGANCE (PARFUM)]), are sequentially added to the previous mixture.

Last, phase E (water [INCI: WATER (AQUA)] and sodium hydroxide [INCI: SODIUM HYDROXIDE]) is incorporated into the previous mixture for pH adjustment to 6.0-6.5.

The entire list of ingredients is presented in Table 13.

TABLE 13

| Phase | INGREDIENT (INCI name) | % weight |
|---|---|---|
| A | WATER (AQUA) | 71.1 |
| A | PROPANEDIOL | 10.0 |
| A | PENTYLENE GLYCOL | 2.0 |
| A | DISODIUM EDTA | 0.2 |
| A1 | CARBOMER | 0.5 |
| A2 | POTASSIUM CETYL PHOSPHATE | 0.5 |
| B | DIISOPROPYL ADIPATE GLYCERYL STEARATE, CETEARYL ALCOHOL, | 5.0 |
| B | POTASSIUM PALMITOYL HYDROLYZED WHEAT PROTEIN | 5.0 |
| B | ETHYLHEXYL COCOATE | 2.5 |
| B | DIMETHICONE | 1.0 |
| B | TOCOPHERYL ACETATE | 0.5 |
| B | PHENOXYETHANOL | 0.5 |
| C | MINERAL OIL (PARAFFINUM LIQUIDUM), WATER (AQUA), ACRYLATES/ACRYLAMIDE CROSSPOLYMER, POLYSORBATE 85 | 1.0 |
| D | FRAGANCE (PARFUM) | 0.2 |
| E | WATER, SODIUM HYDROXIDE | q.s. |

Example 16: In Vivo Study with the Composition of Example 14, for the Assessment of the Rejuvenating Effect in Caucasian Skin Type Female Volunteers The study is carried out during 56 days with measurements at different times. 60 Caucasian female volunteers (20 aged between 18 and 25 years old—group I, 20 aged between 35 and 40 years old—group II, and 20 aged between 50 and 55 years old—group III) are included. Subjects apply the composition described in Example 14 on one half-face and one forearm (left or right) and a placebo cream described in Example 15 on the other half-face and the other forearm. Both creams are applied twice a day (morning and night). The subjects serve as their own reference and results obtained at different times are compared with those obtained at initial time. Moreover, results obtained with the composition of Example 14 are compared with those obtained with placebo cream.

The rejuvenating efficacy of the product is assessed based on two parameters, stratum corneum turnover time and skin roughness:

Stratum corneum turnover time (SCTT) assessment in the volunteers' groups I, II and III. SCTT is understood as the average time for renewal of the stratum corneum cells. A dihydroxyacetone (DHA) solution is applied on a defined area of the volar forearm to stain skin. The composition of Example 14 and placebo (Example 15) cream are applied during a period of 28 days. The disappearance of DHA staining is periodically evaluated (every 4 days) with a colorimeter within this 28-days period of use. A colorimeter is also used to evaluate the color of the skin of an untreated area. The results are shown in table 14.

TABLE 14

Stratum corneum turnover time in days of different areas after 28 days of product application

| | SCTT (days) | | |
|---|---|---|---|
| | Group I | Group II | Group III |
| Composition of Example 14 area | 13.6 | 15.0 | 16.2 |
| Placebo cream of Example 15 area | 14.8 | 16.4 | 18.0 |
| Untreated area | 15.0 | 16.8 | 18.6 |

These results shown in table 14 demonstrate that, after 28 days of application of the composition of Example 14, there is a significant decrease in the SCTT on skin compared to the untreated skin and the skin treated with the placebo.

Skin roughness assessment in the volunteers' groups II and III. The underneath eye area is measured using a real 3D microtopography imaging system (Primos™ lite GFMesstechnik GmbH). Parameter "Sa," defined as the arithmetic mean of the surface roughness (μm) is measured before product application and after 28 and 56 days of product application. Results are shown in Table 15.

TABLE 15

Sa parameter of active and placebo creams after 28 and 56 days of product application.

| | Sa variations (%) | | | |
|---|---|---|---|---|
| | Group II | | Group III | |
| | Composition of Example 14 area | Placebo cream (Example 15) area | Composition of Example 4 area | Placebo cream (Example 15) area |
| [(T + 28 days − T0)/T0] × 100 | −7.9% | 3.0% | −9.8% | 3.9% |
| [(T + 56 days − T0)/T0] × 100 | −10.2% | 2.8% | −13.7% | 1.4% |

These results shown in table 15 demonstrate that, after 28 days of application of the composition of Example 14, there is a significant decrease in the roughness of skin. Moreover, after 56 days of product application skin roughness is even more reduced.

Example 17: In Vivo Study with the Composition of Example 14, for the Assessment of the Skin Radiance in Caucasian Skin Type Female Volunteers The study is carried out during 56 days with measurements at initial time, and after 56 days of product application. 20 Caucasian female volunteers are included. Subjects apply the composition described in Example 14 on face twice a day (morning and night). The subjects serve as their own reference and results obtained at different times are compared with those obtained at initial time.

The efficacy of the product is assessed by:
Luminosity of the skin (parameter L*) or skin radiance measured in macrophotographies using cross-polarized filters. Results are shown in table 16.

TABLE 16

Parameter L* before and after 56 days of product application.

|  | Parameter L* | |
| --- | --- | --- |
|  | T0 | T56 |
| Composition of Example 14 | 47.20 | 47.89 |

These results shown in table 16 prove that, after 56 days of application of the composition of Example 14, there is a significant increase in the luminosity of skin compared to baseline.

One of the consequences of the aging process is the decrease of the skin radiance due to a decrease of the luminosity of the skin. It is demonstrated here that the application of the composition of the Example 14 produces an increase of the skin radiance and, therefore, it makes the skin look rejuvenated.

Example 18: Preparation of a Microemulsion Comprising Peptide DD14024

In an appropriate container the peptide DD14024 is dissolved in water [INCI: WATER (AQUA)] (phase A1), and then a mixture of the ingredients of phase A2 (2-phenoxyethanol [INCI: PHENOXYETHANOL], Structure® XL [INCI: HYDROXYPROPYL STARCH PHOSPHATE], Zemea™ [INCI: PROPANEDIOL], Amigel® [INCI: SCLEROTIUM GUM], and sodium hyaluronate [INCI: SODIUM HYALURONATE]; see Table 17), which had been premixed in a separate recipient, is introduced. The resulting mixture is heated at 70° C. while stirring gently and then Cola® Fax CPE-K [INCI: POTASSIUM CETYL PHOSPHATE] is added (phase A3).

In another recipient, the components of phase B: Schercemol™ DIS Ester [INCI: DIISOPROPYL SEBACATE] and Montanov™ 68 [INCI: CETEARYL ALCOHOL; CETEARYL GLUCOSIDE] are introduced, heating them at 80° C. and stirring the mixture. Phase B is slowly introduced over phase A while intense stirring takes place.

Keeping the temperature at 70-80° C., the sample is homogenized with a titanium probe for 30 seconds.

TABLE 17

| Phase | INGREDIENT (INCI name) | % weight |
| --- | --- | --- |
| A1 | WATER (AQUA) | q.s. 100 |
| A1 | Peptide DD14024 | 0.0010 |
| A2 | PHENOXYETHANOL | 2.7382 |
| A2 | HYDROXYPROPYL STARCH PHOSPHATE | 0.6570 |
| A2 | PROPANEDIOL | 5.4764 |
| A2 | SCLEROTIUM GUM | 0.3285 |
| A2 | SODIUM HYALURONATE | 0.0109 |
| A3 | POTASSIUM CETYL PHOSPHATE | 0.5476 |
| B | DIISOPROPYL SEBACATE | 10.9500 |
| B | [CETEARYL ALCOHOL; CETEARYL GLUCOSIDE] | 4.3811 |

Example 19: Preparation of a Lipid Nanoparticle Composition Comprising the Microemulsion of Example 18

The microemulsion prepared in Example 18 is introduced into an appropriate recipient (phase A).

Separately, phase B (see TABLE 18) is prepared by dissolving N-Hance® CG-17 Cationic Guar [INCI: GUAR HYDROXYPROPYLTRIMONIUM CHLORIDE; WATER (AQUA)] in water [INCI: WATER (AQUA)]. Phase B is added to phase A under intense stirring.

Components of phase C (Structure® XL [HYDROXYPROPYL STARCH PHOSPHATE] and Amigel® [INCI: SCLEROTIUM GUM]) and phase D (Heliogel™ [INCI: SODIUM ACRYLATES COPOLYMER; HYDROGENATED POLYISOBUTENE; LECITHIN; POLYGLYCERYL-10 STEARATE; SUNFLOWER (HELIANTHUS ANNUUS) SEED OIL; TOCOPHEROL]) are added slowly and one by one under intense stirring.

TABLE 18

| Phase | INGREDIENT (INCI name) | % weight |
| --- | --- | --- |
| A | Microemulsion of Example 18 | q.s. 100% |
| B | [GUAR HYDROXYPROPYLTRIMONIUM CHLORIDE; WATER (AQUA)] | 0.20 |
| B | WATER (AQUA) | 6.00 |
| C | HYDROXYPROPYL STARCH PHOSPHATE | 1.50 |
| C | SCLEROTIUM GUM | 0.75 |
| D | [SODIUM ACRYLATES COPOLYMER; HYDROGENATED POLYISOBUTENE; LECITHIN; POLYGLYCERYL-10 STEARATE; SUNFLOWER (*HELIANTHUS ANNUUS*) SEED OIL; TOCOPHEROL] | 0.25 |

Example 20: Preparation of Liposomes Comprising Peptide DD14024

In an appropriate container, phase A is prepared by dissolving peptide DD14024 in water [INCI: WATER (AQUA)]. Zemea™ [INCI: PROPANEDIOL] and 2-phenoxyethanol [INCI: PHENOXYETHANOL] (phase B) are added to phase A.

When all the previous components are dissolved, lecithin [INCI: LECITHIN] (phase C) is added little by little and under intense stirring, until complete dispersion. The finally obtained composition is shown in TABLE 19.

TABLE 19

| Phase | INGREDIENT (INCI name) | % weight |
| --- | --- | --- |
| A | WATER (AQUA) | q.s. 100% |
| A | Peptide DD14024 | 0.0010 |
| B | PROPANEDIOL | 8.5000 |
| B | PHENOXYETHANOL | 0.9050 |
| E | LECITHIN | 0.5000 |

The sample is homogenized with a titanium probe for 30 seconds.

Example 21: Preparation of Liposomes of Example 20 Bound to Cationic Polymers The liposomes obtained in Example 20 are added to SENSOMER® CT-50 [INCI: WATER (AQUA); STARCH HYDROXYPROPYLTRIMONIUM CHLORIDE; UREA; SODIUM LACTATE; SODIUM CHLORIDE; SODIUM BENZOATE] at a liposomes:cationic polymer ratio of 95:5 (w/w) under slow stirring.

The following Sequence Listing is incorporated herein by reference in its entirety.

The invention claimed is:

1. A compound of general formula (I):

$$R_1\text{-}AA_1\text{-}AA_2\text{-}AA_3\text{-}AA_4\text{-}AA_5\text{-}AA_6\text{-}R_2 \quad \text{(I)(SEQ ID NO.33)},$$

its stereoisomers and/or its cosmetically or pharmaceutically acceptable salts, wherein:

$AA_1$ is selected from the group consisting of Gln, Glu, Asp and Asn;

$AA_2$ is selected from the group consisting of Glu, Gln and Asp;

$AA_3$ is selected from the group consisting of Met, Ile and Leu;

$AA_4$ is selected from the group consisting of Arg, Lys and Orn;

$AA_5$ is selected from the group consisting of Met, Leu, Ile and Val;

$AA_6$ is selected from the group consisting of Gln, Asn and Glu;

$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids, with the proviso that the compound is not Ac-Asn-Glu-Met-Arg-Met-Gln-OH (Ac-[SEQ ID NO.30]-OH), Ac-Gln-Glu-Met-Arg-Leu-Gln-OH (Ac-[SEQ ID NO.31]-OH), or Palm-Gln-Glu-Met-Arg-Met-Asn-OH (Palm-[SEQ ID NO.32]-OH).

2. A compound according to claim 1, wherein:
(i) $AA_1$ is Gln, $AA_2$ is Glu, $AA_3$ is Met, $AA_4$ is Arg, $AA_5$ is Met, and $AA_6$ is Gln, or
(ii) $AA_1$ is Gln, $AA_2$ is Glu, $AA_3$ is Met, $AA_4$ is Arg, $AA_5$ is Met and $AA_6$ is Gln, and 1 to 3 of $AA_1$, $AA_2$, $AA_3$, $AA_4$, $AA_5$ and $AA_6$ are replaced providing that:
when $AA_1$ is replaced, it is replaced by an amino acid selected from the group consisting of Glu, Asp and Asn;
when $AA_2$ is replaced, it is replaced by an amino acid selected from the group consisting of Gln and Asp;
when $AA_3$ is replaced, it is replaced by an amino acid selected from the group consisting of Ile and Leu;
when $AA_4$ is replaced, it is replaced by an amino acid selected from the group consisting of Lys and Orn;
when $AA_5$ is replaced, it is replaced by an amino acid selected from the group consisting of Leu, Ile and Val; and
when $AA_6$ is replaced, it is replaced by an amino acid selected from the group consisting of Asn and Glu.

3. A compound according to claim 2, wherein three of $AA_1$, $AA_2$, $AA_3$, $AA_4$, $AA_5$ and $AA_6$ are replaced.

4. A compound according to claim 3, wherein $AA_1$, $AA_3$ and $AA_5$ are replaced or $AA_2$, $AA_4$ and $AA_6$ are replaced.

5. A compound according to claim 2, wherein two of $AA_1$, $AA_2$, $AA_3$, $AA_4$, $AA_5$ and $AA_6$ are replaced.

6. A compound according to claim 5, wherein $AA_2$ and $AA_6$ are replaced, $AA_4$ and $AA_5$ are replaced, $AA_1$ and $AA_2$ are replaced, or $AA_1$ and $AA_3$ are replaced.

7. A compound according to claim 2, wherein one of $AA_1$, $AA_2$, $AA_3$, $AA_4$, $AA_5$ and $AA_6$ is replaced.

8. A compound of general formula:

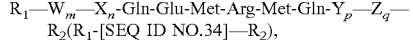

$R_1$—$W_m$—$X_n$-Gln-Glu-Met-Arg-Met-Gln-$Y_p$—$Z_q$—$R_2$($R_1$-[SEQ ID NO.34]—$R_2$), its stereoisomers and/or its cosmetically or pharmaceutically acceptable salts, wherein:
m, n, p and q are each independently 0 or 1;
$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ and $R_2$ are not α-amino acids.

9. A compound according to claim 1, wherein $R_1$ is selected from H, acetyl, myristoyl and palmitoyl and $R_2$ is selected from —OH, —$NH_2$ and —$NHR_3$, wherein $R_3$ is a $C_6$ to $C_{18}$ alkyl group.

10. A cosmetic or pharmaceutical composition which comprises at least one compound of general formula (I), its stereoisomers and/or its cosmetically or pharmaceutically acceptable salts, according to claim 1 and at least one cosmetically or pharmaceutically acceptable excipient or adjuvant.

11. A composition according to claim 10, wherein said compound of general formula (I), its stereoisomers and/or its cosmetically or pharmaceutically acceptable salts, is incorporated into a cosmetically or pharmaceutically acceptable delivery system or sustained release system selected from the group consisting of liposomes, mixed liposomes, oleosomes, niosomes, ethosomes, milliparticles, microparticles, nanoparticles, solid lipid nanoparticles, nanostructured lipid carriers, sponges, cyclodextrins, vesicles, micelles, mixed micelles of surfactants, surfactant-phospholipid mixed micelles, millispheres, microspheres, nanospheres, lipospheres, millicapsules, microcapsules, nanocapsules, microemulsions and nanoemulsions or is absorbed onto a solid organic polymer or solid mineral support selected from the group consisting of talc, bentonite, silica, starch and maltodextrin.

12. A composition according to claim 10, wherein said composition is in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays, aerosols, capsules, gelatin capsules, soft capsules, hard capsules, tablets, sugar coated tablets, pills, powders, granules, chewing gum, solutions, suspensions, emulsions, syrups, elixirs, jellies and gelatins.

13. A compound of general formula (I):

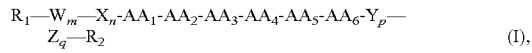

$R_1$—$W_m$—$X_n$-$AA_1$-$AA_2$-$AA_3$-$AA_4$-$AA_5$-$AA_6$-$Y_p$—$Z_q$—$R_2$     (I), its stereoisomers and/or its cosmetically or pharmaceutically acceptable salts, wherein:
W, X, Y and Z are each independently an amino acid;
m, n, p and q are each independently 0 or 1;
$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ and $R_2$ are not α-amino acids,
wherein:
$AA_1$ is Gln, $AA_2$ is Glu, $AA_3$ is Met, $AA_4$ is Arg, $AA_5$ is Met, and $AA_6$ is Gln (SEQ ID NO.1), or when $AA_1$ is Gln, $AA_2$ is Glu, $AA_3$ is Leu, $AA_4$ is Arg, $AA_5$ is Met, and $AA_6$ is Gln (SEQ ID NO.11).

14. A compound of general formula (I):

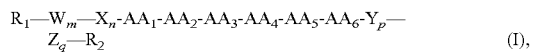

its stereoisomers and/or its cosmetically or pharmaceutically acceptable salts, wherein:
W, X, Y and Z are each independently an amino acid;
m, n, p and q are each independently 0 or 1;
$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ and $R_2$ are not α-amino acids, and
wherein $W_m$—$X_n$-$AA_1$-$AA_2$-$AA_3$-$AA_4$-$AA_5$-$AA_6$-$Y_p$—$Z_q$ is selected from:

```
                                 SEQ ID NO. 1
Gln-Glu-Met-Arg-Met-Gln,

SEQ ID NO. 2
Asp-Glu-Met-Arg-Met-Gln,

SEQ ID NO. 3
Glu-Glu-Met-Arg-Met-Gln,

SEQ ID NO. 4
Gln-Gln-Met-Arg-Met-Gln,

SEQ ID NO. 5
Gln-Glu-Met-Lys-Met-Gln,

SEQ ID NO. 6
Gln-Glu-Met-Orn-Met-Gln,

SEQ ID NO. 7
Gln-Glu-Met-Arg-Met-Glu,

SEQ ID NO. 8
Gln-Glu-Met-Arg-Met-Asn,

SEQ ID NO. 10
Gln-Asp-Met-Arg-Met-Gln,

SEQ ID NO. 11
Gln-Glu-Leu-Arg-Met-Gln,
```

```
                                 SEQ ID NO. 12
Gln-Glu-Ile-Arg-Met-Gln,

SEQ ID NO. 13
Gln-Glu-Met-Arg-Ile-Gln,

SEQ ID NO. 14
Gln-Glu-Met-Arg-Leu-Gln,

SEQ ID NO. 15
Glu-Glu-Ile-Arg-Met-Gln,

SEQ ID NO. 16
Asp-Gln-Met-Arg-Met-Gln,

SEQ ID NO. 17
Glu-Gln-Met-Arg-Met-Gln,

SEQ ID NO. 18
Gln-Glu-Met-Lys-Leu-Gln,

SEQ ID NO. 19
Gln-Asp-Met-Arg-Met-Asn,

SEQ ID NO. 20
Asn-Glu-Ile-Arg-Val-Gln,

SEQ ID NO. 21
Gln-Asp-Met-Lys-Met-Asn,

SEQ ID NO. 22
Pro-Gln-Glu-Met-Arg-Met-Gln,

SEQ ID NO. 23
Gln-Glu-Met-Arg-Met-Gln-Val-Tyr,
and
                                 SEQ ID NO. 24
Ser-Gln-Glu-Met-Arg-Met-Gln-Thr.
```

15. A compound of general formula (I):

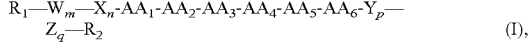

its stereoisomers and/or its cosmetically or pharmaceutically acceptable salts, wherein:
W, X, Y and Z are each independently an amino acid;
m, n, p and q are each independently 0 or 1;
$R_1$ is selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ and $R_2$ are not α-amino acids, and
wherein $W_m$—$X_n$-$AA_1$-$AA_2$-$AA_3$-$AA_4$-$AA_5$-$AA_6$-$Y_p$—$Z_q$ is selected from:

```
Ac-Gln-Glu-Met-Arg-Met-Gln-OH          (Ac-[SEQ ID NO. 1]-OH),
H-Gln-Glu-Met-Arg-Met-Gln-OH           (H-[SEQ ID NO. 1]-OH),
Palm-Gln-Glu-Met-Arg-Met-Gln-OH        (Palm-[SEQ ID NO. 1]-OH),
Ac-Gln-Glu-Met-Arg-Met-Gln-NH2         (Ac-[SEQ ID NO. 1]-NH2),
Ac-Gln-Glu-Met-Arg-Met-Gln-NHC6H13     (Ac-[SEQ ID NO. 1]-NHC6H13),
Myr-Gln-Glu-Met-Arg-Met-Gln-NH2        (Myr-[SEQ ID NO. 1]-NH2),
Ac-Asp-Glu-Met-Arg-Met-Gln-OH          (Ac-[SEQ ID NO. 2]-OH),
Ac-Glu-Glu-Met-Arg-Met-Gln-OH          (Ac-[SEQ ID NO. 3]-OH),
Ac-Gln-Gln-Met-Arg-Met-Gln-OH          (Ac-[SEQ ID NO. 4]-OH),
Ac-Gln-Glu-Met-Lys-Met-Gln-OH          (Ac-[SEQ ID NO. 5]-OH),
Ac-Gln-Glu-Met-Orn-Met-Gln-OH          (Ac-[SEQ ID NO. 6]-OH),
Ac-Gln-Glu-Met-Arg-Met-Glu-OH          (Ac-[SEQ ID NO. 7]-OH),
Ac-Gln-Glu-Met-Arg-Met-Asn-OH          (Ac-[SEQ ID NO. 8]-OH),
Myr-Glu-Glu-Met-Arg-Met-Gln-OH         (Myr-[SEQ ID NO. 3]-OH),
Ac-Gln-Asp-Met-Arg-Met-Gln-NHC6H13     (Ac-[SEQ ID NO. 10]-NHC6H13),
Palm-Gln-Glu-Leu-Arg-Met-Gln-OH        (Palm-[SEQ ID NO. 11]-OH),
H-Gln-Glu-Ile-Arg-Met-Gln-NH2          (H-[SEQ ID NO. 12]-NH2),
H-Gln-Glu-Met-Arg-Ile-Gln-NH2          (H-[SEQ ID NO. 13]-NH2),
H-Gln-Glu-Met-Arg-Leu-Gln-NH2          (H-[SEQ ID NO. 14]-NH2),
Ac-Glu-Glu-Ile-Arg-Met-Gln-NHC16H33    (Ac-[SEQ ID NO. 15]-NHC16H33),
Ac-Asp-Gln-Met-Arg-Met-Gln-OH          (Ac-[SEQ ID NO. 16]-OH),
Ac-Glu-Gln-Met-Arg-Met-Gln-OH          (Ac-[SEQ ID NO. 17]-OH),
Ac-Gln-Glu-Met-Lys-Leu-Gln-OH          (Ac-[SEQ ID NO. 18]-OH),
H-Gln-Asp-Met-Arg-Met-Asn-NH2          (H-[SEQ ID NO. 19]-NH2),
Ac-Asn-Glu-Ile-Arg-Val-Gln-OH          (Ac-[SEQ ID NO. 20]-OH),
Ac-Gln-Asp-Met-Lys-Met-Asn-OH          (Ac-[SEQ ID NO. 21]-OH),
Ac-Pro-Gln-Glu-Met-Arg-Met-Gln-OH      (Ac-[SEQ ID NO. 22]-OH),
Ac-Gln-Glu-Met-Arg-Met-Gln-Tyr-OH      (Ac-[SEQ ID NO. 26]-OH),
Ac-Gln-Glu-Met-Arg-Met-Gln-Thr-NH2     (Ac-[SEQ ID NO. 27]-NH2),
Ac-Pro-Val-Gln-Glu-Met-Arg-Met-Gln-OH  (Ac-[SEQ ID NO. 28]-OH),
Ac-Gln-Glu-Met-Arg-Met-Gln-Val-Tyr-OH  (Ac-[SEQ ID NO. 29]-OH), and
Ac-Ser-Gln-Glu-Met-Arg-Met-Gln-Thr-NH2 (Ac-[SEQ ID NO. 24]-NH2).
```

16. A method for cosmetic, non-therapeutic treatment and/or non-therapeutic care of the skin, hair, and/or nails which comprises administering to the skin, hair, and/or nails of a subject a cosmetically effective quantity of a compound according claim 1.

17. A method for alleviation of symptoms of skin aging which comprises administering to the skin of a subject a cosmetically effective quantity of a compound according to claim 1.

18. A method for alleviation of symptoms of skin aging which comprises administering to the skin of a subject a cosmetically effective quantity of a compound according to claim 8.

19. A method for alleviation of symptoms of skin aging which comprises administering to the skin of a subject a cosmetically effective quantity of a compound according to claim 13.

20. A method for alleviation of symptoms of skin aging which comprises administering to the skin of a subject a cosmetically effective quantity of a compound according to claim 14.

21. A method for alleviation of symptoms of skin aging which comprises administering to the skin of a subject a cosmetically effective quantity of a compound according to claim 15.

* * * * *